(12) United States Patent
Kimura

(10) Patent No.: US 8,126,237 B2
(45) Date of Patent: Feb. 28, 2012

(54) MAGNETIC RESONANCE IMAGING AND CORRECTING DEVICE

(75) Inventor: Tokunori Kimura, Yaita (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 1435 days.

(21) Appl. No.: 10/596,052

(22) PCT Filed: Nov. 11, 2005

(86) PCT No.: PCT/JP2005/020736
§ 371 (c)(1),
(2), (4) Date: May 26, 2006

(87) PCT Pub. No.: WO2006/051911
PCT Pub. Date: May 18, 2006

(65) Prior Publication Data
US 2009/0010514 A1 Jan. 8, 2009

(30) Foreign Application Priority Data

Nov. 12, 2004 (JP) .................................. 2004-329783

(51) Int. Cl.
*G06K 9/00* (2006.01)
*A61B 5/05* (2006.01)
(52) U.S. Cl. ........................................ 382/131; 600/410
(58) Field of Classification Search .................. 382/131
See application file for complete search history.

(56) References Cited

U.S. PATENT DOCUMENTS

| 4,945,916 A * | 8/1990 | Kretschmer et al. .......... 600/484 |
| 5,200,700 A | 4/1993 | Glover et al. |
| 5,251,629 A * | 10/1993 | Koizumi et al. .............. 600/410 |
| 5,818,231 A * | 10/1998 | Smith .......................... 324/309 |
| 6,188,922 B1 * | 2/2001 | Mistretta et al. .............. 600/419 |
| 2003/0171668 A1* | 9/2003 | Tsujino et al. ................ 600/407 |
| 2003/0179918 A1* | 9/2003 | Kohler .......................... 382/131 |
| 2004/0056660 A1* | 3/2004 | Yatsui et al. .................. 324/309 |
| 2008/0200800 A1* | 8/2008 | Kuhara et al. ................. 600/421 |
| 2008/0281186 A1* | 11/2008 | Kuhara ......................... 600/413 |

FOREIGN PATENT DOCUMENTS

| JP | 6-47021 | 2/1994 |
| JP | 2000-157507 | 6/2000 |
| JP | 2000157507 A * | 6/2000 |

(Continued)

OTHER PUBLICATIONS

Machine generated translation of JP 2000157507 A, pp. 1-6.*

(Continued)

*Primary Examiner* — David Zarka
(74) *Attorney, Agent, or Firm* — Nixon & Vanderhye PC

(57) ABSTRACT

An image data correcting device has a movement information acquiring section, a correcting section and a synthesizing section. The movement information acquiring section acquires movement information showing a spatial distribution of the magnitude of a movement in the real space of an image pickup part of a detected body. The correcting section makes a correction different from that of a second area in a first area of image data collected by a scan of magnetic resonance imaging on the basis of the movement information. The synthesizing section synthesizes respective image data of the first area and the second area corrected by the correcting section.

30 Claims, 15 Drawing Sheets

FOREIGN PATENT DOCUMENTS

| JP | A 2000-157507 | 6/2000 |
|---|---|---|
| JP | 2002-301044 | 10/2002 |
| JP | A 2002-301044 | 10/2002 |
| JP | 2004-73538 | 3/2004 |

OTHER PUBLICATIONS

Edelstein et al., Spin-Warp NMR Imaging and Applications to Human Whole-Body Imaging, Physics in Medicine and Biology, vol. 25, pp. 751-756, 1980.*

Detailed Description, computer generation, JP 2000-157507, pp. 1-6, Jan. 5, 2010.*

International Search Report of PCT/JP2005/020736, mailed Feb. 14, 2006.

Bornstedt et al., "Slice Dependent Correction (SDC): An Extension to Motion Adapted Real Time Navigator Correction", Proc. Intl. Soc. Mag. Reson. Med. 7, 1999, p. 1997.

Ward et al., "Use of Multi-Channel Coil Sensitivities for Improved Detection of Motion with Orbital Navigator Echoes", Proc. Intl. Soc. Mag. Med. 11, 2004, p. 2150.

Miller et al., "Nonlinear Phase Correction for Navigated Diffusion Imaging", Magnetic Resonance in Medicine, vol. 50, No. 2, Aug. 2003, pp. 343-353.

Ehman et al., "Adaptive Technique for High-Definition MR Imaging of Moving Structures", Magnetic Resonance Imaging, vol. 173, No. 1, Radiology, Oct. 1989.

Ordidge et al., "Correction of Motional Artifacts in Diffusion-Weighted MR Images Using Navigator Echoes", Magnetic Imaging, vol. 12, No. 1, pp. 455-460, 1994.

Wang et al., "Navigator-Echo-Based Real-Time Respiratory Gating and Triggering for Reduction of Respiration Effects in Three-Dimensional Coronary MR Angiograph", Cardiac Radiology, vol. 198, No. 1, Jan. 1996.

Pipe, "Motion Correction With Propeller MRI: Application to Head Motion and Free-Breathing Cardiac Imaging", Magnetic Resonance in Medicine 42:963-969 (1999(.

McGee et al., "The Shoulder:Adaptive Motion Correction of MR Images", Musculoskeletal Radiology,vol. 205, No. 2, Nov. 1997.

Miller et al., "Nonlinear Phase Correction for Navigated Diffusion Imaging", Magnetic Resonance in Medicine 50:343-353 (2003).

Manke et al., "Novel Prospective Respiratory Motion Correction Approach for Free-Breathing Coronary MR Angiography Using a Patient-Adapted Affine Motion Model", Magnetic Resonance in Medicine 50:122-131 (2003).

Langenberger et al., "Nonlinear Motion Artifact Reduction in Event-Triggered Gradient-Echo FMRI", Magnetic Resonance Imaging, vol. 15, No. 2, pp. 163-167, 1997.

Notification of Transmittal of Translation of the International Preliminary Report on Patentability (Form PCT/IB/338) mailed May 24, 2007 in International Application No. PCT/JP2005/020736.

International Preliminary Report on Patentability (Form PCT/IB/373) issued May 15, 2007 in International Application No. PCT/JP2005/020736 together with an English translation of the Written Opinion of the International Searching Authority.

Office Action dated Mar. 14, 2008 in CN Application No. 2005800017463.

Office Action dated Jul. 12, 2011 in JP 2006-519655.

* cited by examiner

PULSE SEQUENCE FOR SPIN WARP AND NAVIGATOR ECHO-#1
(IMAGING: R0: x, 1D LINE BY LINE PHASE MEASUREMENT
MODE OF MOVING IN y DIRECTION)

PULSE SEQUENCE FOR SPIN WARP AND NAVIGATOR ECHO-#2
(IMAGING: R0: x, 0'TH ORDER PHASE MEASUREMENT
OF MOVING IN y DIRECTION)

PROCESSING FLOW DIAGRAM OF NONLINEAR MOTION CORRECTION USING 1D NAVIGATOR ECHO (CASE USING SINGLE COIL)

WINDOW EXAMPLE OF THREE DIVISIONS OF SPATIAL REGION IN PROJECTION PROFILE MEASURING MODE

PROCESSING FLOW DIAGRAM OF NONLINEAR MOTION CORRECTION USING 1D NAVIGATOR ECHO (PROCESSING FLOW OF CASE USING MULTICOIL)

MOTION DISPLACEMENTS
OF THREE DIRECTIONS

FIG. 18
SINGLE-COIL IMAGING
(a) 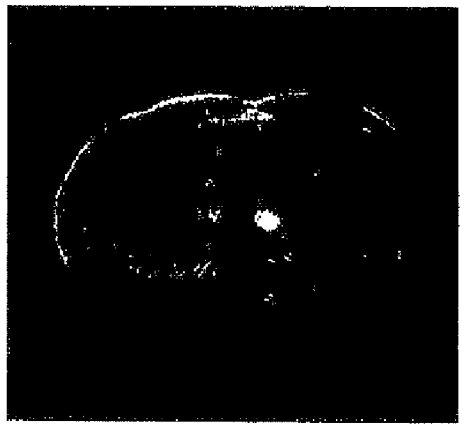  (b) 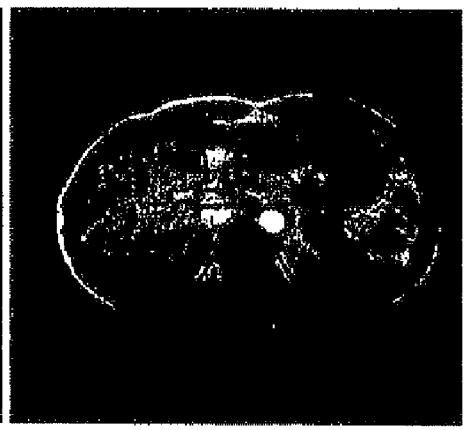
2 SW (INCLUDING AIR) CORRECTION   3 SW (INCLUDING AIR) CORRECTION
FIG. 19
MULTI-COIL IMAGING
(a)   (b) 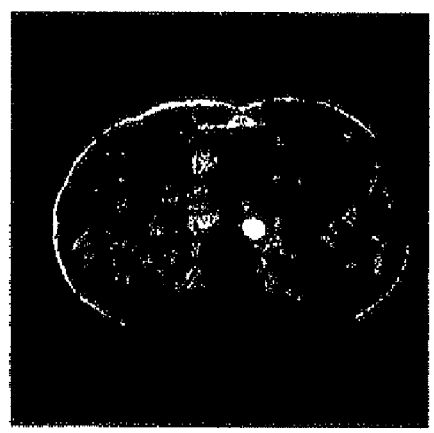
NO SW CORRECTION   +2 SW CORRECTION

MAGNETIC RESONANCE IMAGING AND CORRECTING DEVICE

This application is the US national phase of international application PCT/JP2005/020736, filed 11 Nov. 2005, which designated the U.S. and claims priority of JP 2004-329783, filed 12 Nov. 2004, the entire contents of each of which are hereby incorporated by reference.

TECHNICAL FIELD

The present invention relates to a magnetic resonance imaging device, an image data correcting device and an image data correcting method for obtaining a magnetic resonance (MR) image of a detected body by utilizing a magnetic resonance phenomenon. In particular, the present invention relates to a magnetic resonance imaging device, an image data correcting device and an image data correcting method for executing a correction of collecting data spatially ununiformly deteriorated by a nonlinear movement of the detected body when magnetic resonance imaging using a spin warp method, a spiral method, a radial method, etc. for collecting data filled in a k-space by performing a scan of a multi-shot is performed.

BACKGROUND ART

The magnetic resonance imaging is now used as one of important medical modalities in a medical spot. A system for executing this magnetic resonance imaging is called the magnetic resonance imaging device. A high frequency magnetic field is applied to the detected body, and the magnetic resonance phenomenon is generated in a magnetized spin within the detected body. An echo signal generated by this magnetic resonance phenomenon is collected. Such operations are executed under a time series. An MR image of the detected body is basically obtained by processing this echo signal (including reconstruction processing). Such a series of operations is called a scan.

In this magnetic resonance imaging, it is not preferable to move the detected body (including a body movement due to beating and breathing) during this scan. Such a movement becomes a motion artifact and deteriorates the quality of the reconstructed MR image. Therefore, the restraint of the motion artifact is an important technical theme in the magnetic resonance imaging.

A method using an inclining magnetic field pulse called a navigator is known as one of methods for restraining the motion artifact when the magnetic resonance imaging is performed by using a pulse sequence of a multi-shot type. In this method, the movement of the detected body is monitored by using the echo signal (also called the navigator echo signal, or briefly called the navi echo) collected by applying this navigator, and the collecting data are corrected on the basis of this monitor information (see non-patent literatures 1 to 8).

As can be seen from non-patent literatures 1, 2, the mode of data for monitoring the movement was first a one-dimensional projecting profile. In contrast to this, recently, as can be seen from non-patent literatures 4, 5, 7, a system for two-dimensionally monitoring and correcting the movement during the scan is also proposed.

However, in the methods reported so far, a rigid movement of a head portion, etc., i.e., parallel translation and a rotating movement as a rigid body are set to objects. With respect to a movement having a spatial distribution in the movement, i.e., a nonrigid movement, a movement collected within a voxel as in diffusion imaging is set to an object (see non-patent literature 7). It is merely reported in application (see patent literature 9) able to separate a movement component in a time series image of the head portion at a spatial frequency. However, it is not reported in a structure in which the nonrigid movement for spatially ununiformly moving (shifting) each position forming the abdominal part as in the movement (motion) of a breathing property of the abdominal part, etc. is set to an object.

The technical reasons for this unreport will be explained. When the rigid body is shifted in a linear position in a direction parallel with this inclining magnetic field under an inclining magnetic field of constant intensity and constant time in the magnetic resonance imaging, this position shift is proportional to a shift amount of an average phase in the r(real)-space (exactly, it is also called a hybrid space (h-space) since it is the r-space on only one side axis and is the k-space on the other axis). Accordingly, when the shift is nonlinear every position, i.e., the shift amount every position is different, it is impossible to know the spatial distribution of the movement even when the average phase is calculated.

On the one hand, the nonlinear movement can be corrected if the spatial distribution of the position shift caused by the movement can be measured in accordance with a changing frequency. It is necessary to newly apply a navigator pulse every shot as well as the pulse sequence for imaging so as to measure the movement. However, in the case of this technique, time-like restriction is added to the navi echo collected to calculate a two-dimensional distribution of the movement. On the other hand, since it is comparatively easy to measure the movement as one dimension as projection data of a certain axis direction, there are many reports. However, the application of this technique is limited to the linear movement as the rigid body, and it is difficult to cope with the nonlinear movement.

The case for measuring the navi echo as the one-dimensional projection data will be described in detail. In this case, normally, in addition to the echo for imaging, the navi echo of a read-out direction provided when a phase encode amount is set to zero every shot and the navi echo is collected while applying the inclining magnetic field in the read-out direction of the imaging, i.e., projection data in the phase encode direction are acquired and corrected. In this case, with respect to the navi eco of the read-out direction, the projection data integrated along the phase encode direction can be acquired with respect to each position of the read-out direction in timing considered to make the same movement as the collecting time of the echo for imaging. Therefore, the echo for imaging can be corrected correspondingly to each line of each projection data in the read-out direction. Accordingly, it is also possible to cope with the nonlinear movement in the read-out direction to a certain extent (see non-patent literature 1).

However, in the case of the navi echo collection of the read-out direction at the imaging time, the nonlinear correction wrath respect to the movement in the phase encode direction is impossible. Accordingly, the navi echo of the phase encode direction is used. However, in this case, differing from the navi echo of the read-out direction, the echo data for imaging acquired in the same moving state as the navi echo are data on only a line acquired in the same shot as the navi echo. Therefore, in the phase encode direction of the echo for imaging, data acquired in the moving state different every shot are mixed. Therefore, even when these data are corrected to data of the r-space (also called the hybrid-space (h-space)) by performing the Fourier transform in the phase encode direction as they are, it does not correspond to the line of the navi echo Fourier-transformed. Accordingly, it is difficult to make the nonlinear movement correction of the phase encode direction by the navi echo of the phase encode direction. However, in this case, the correction can be also made if zero is put close to a position except for the shot corresponding to the navi echo in the k-space of the echo for imaging, and the data transformed to the hybrid space (h-space) are corrected every shot and are synthesized.

Thus, it is possible to measure the shift of the position due to a spatially ununiform movement and the distribution of the phase in principle, and make the correction in the r-space every voxel. However, a measuring technique (a pulse sequence or an external monitor) of the movement different from the original imaging technique (pulse sequence) is required. Accordingly, it is difficult to make the measurement itself in time and technique. In addition to this, it is necessary to execute the measurement and the correction by a shot number with respect to one image. Therefore, as the number of shots is increased, an arithmetic amount becomes enormous and nonrealistic. In a case using a one-dimensional distribution as projection, the movement of the read-out direction of imaging can be also made in nonlinearity by measuring the position shift every projection line in the r-space and reversely performing the shift, but the arithmetic amount is increased. When the nonlinear movement of the phase encode direction of imaging is set to an object, the arithmetic amount is further increased. In this case, no interpolation is required in the correction in the k-space. However, in the correction in the real space, the interpolation is required in the correction of the shift in a degree of 1 pixel or less.

This situation will be described in detail with the spin warp method of the multi-shot as an example. In the case of the spin warp method of the multi-shot; collective data of a certain line number are acquired by performing division in the phase encode direction in the k-space every one shot. Therefore, data influenced by the movement different every shot are mixed in the k-space. In the nonlinear correction of the spatial positions turning-back is caused in the image space even when a distribution $\Delta Y(y,n)$ of the nonlinear shift every position y is measured in the r-space every shot, and the corrected image is repeatedly made. Therefore, portions of different movements are overlapped and cannot be distinguished so that no correction can be made in principle. With respect to the measurement itself, in the case of the nonlinear movement, it is very difficult to identify the position relation before and after the movement of the same portion every voxel. In particular, in the case of the normal spin warp method, data every one line are collected every shot and are converted into data of the r-space every line, and the shift amount every position y is then measured. Thereafter, the position correction is made every position y. Accordingly, the arithmetic amount becomes enormous in both the measurement and the correction.

On the other hand, in the k-space, the measurement and the correction can be easily made until the phase distributions of spatial zeroth and first orders. The position shift in the r-space becomes a phase shift in the k-space. Therefore, it is sufficient to arithmetically calculate the product of a phase term at the same point of the k-space, and the correction of a subpixel or less in the r-space can be also made. Therefore, the arithmetic calculation in the k-space is desirable in consideration of convenience of processing. However, in the k-space, it is limited to the measurement and correction of the linear motion, and the measurement and correction of the spatial nonlinear motion are difficult.

Non-patent literature 1: Ehman R L, Felmlee, J P. Radiology. Adaptive technique for high-definition MR imaging of moving structures. Radiology 1989 October; 173(1): 255-63.

Non-patent literature 2: Ordidge R J, Helpern J A, Qing Z X, Knight R A, Nagesh V. Correction of motional artifacts in diffusion-weighted MR images using navigator echoes. Magn Reson Imaging. 1994; 12(3): 455-60.

Non-patent literature 3: Wang. Y, Rossman P J, Grimm R C, Riederer S J, Ehman R L, Navigator-echo-based real-time respiratory gating and triggering for reduction of respiration effects in three-dimensional coronary MR angiography. Radiology. 1996 January; 198(1): 55-60.

Non-patent literature 4: Pipe J G. Motion correction with PROPELLER MRI: application to head motion and free-breathing cardiac imaging. Magn Reson Med. 1999 November; 42(5): 963 to 9.

Non-patent Literature 5: Pipe J G, Farthing V G, Forbes K P. Multishot diffusion-weighted FSE using PROPELLER MRI. Magn Reson Med 2002 March; 47(3): 621.

Non-patent literature 6: McGee K P, Grimm R C, Felmlee J P, Rydberg J R, Riederer S J, Ehman R L. The shoulder: adaptive motion correction. Radiology. 1997 November; 205(2): 541-5.

Non-patent literature 7: Miller K L, Pauly J M. Nonlinear phase correction for navigated diffusion imaging. Magn Reson Med. 2003 August; 50(2): 343-53.

Non-patent literature 8: Manke D, Nehrke K, Bornert P. Novel prospective respiratory motion correction approach for free-breathing coronary MR angiography using a patient-adapted affine motion model. Magn Reson Med. 2003 July; 50(1): 122-31.

Non-patent literature 9: Langenberger K W, Moser E. Nonlinear motion artifact reduction in event-triggered gradient-echo FMRI. Magn Reson Imaging. 1997; 15(2): 163-7.

DISCLOSURE OF THE INVENTION

The present invention is made in consideration of the above situation of the prior art, and its object is to provide a magnetic resonance imaging device, an image data correcting device and an image data correcting method able to obtain an MR image by comparatively simply correcting echo data spatially ununiformly deteriorated and collected by the nonlinear movement of an image pickup part at high speed when the image is obtained from data of the k-space particularly collected and filled by using the pulse sequence of the multi-shot type in the magnetic resonance imaging.

To achieve the above object, an image data correcting device in the present invention comprises:

a movement information acquiring section for acquiring movement information showing a spatial distribution of the magnitude of a movement in the real space of an image pickup part of a detected body;

a correcting section for making a correction different from that of a second area in a first area of image data of the image pickup part of the detected body collected by a scan of magnetic resonance imaging on the basis of the movement information; and a synthesizing section for synthesizing respective image data of the first area and the second area corrected by the correcting section.

To achieve the above object, an image data correcting device in the present invention also comprises:

a correcting section for making a correction different from that of a second area in a first area of image data of an image pickup part of a detected body collected by a scan of magnetic resonance imaging on the basis of movement information showing a spatial distribution of the magnitude of a movement in the real space of the image pickup part; and a synthesizing section for synthesizing the respective image data of the first area and the second area corrected by the correcting section.

To achieve the above object, an image data correcting device in the present invention also comprises:

a first data converting section for converting data of a first space in a first area and a second area of an image pickup part of a detected body into data of a second space in a third area and a fourth area;

a correcting section for making a correction different from that of the fourth area with respect to the data of the second space in the third area;

a synthesizing section for synthesizing the data of the second space in the third area after the correction, and the data of the second space in the fourth area; and a second converting section for converting the data of the second space after the synthesis into data of the first space.

To achieve the above object, an image data correcting device in the present invention also comprises:

a first data converting section for converting data of at least one area among data of a first space of plural areas in an image pickup part of a detected body into data of a second space;

a correcting section for correcting the data of the second space; and a second data converting section for converting the data of the second space after the correction into data of the first space.

To achieve the above object, an image data correcting method in the present invention comprises:

a step for acquiring movement information showing a spatial distribution of the magnitude of a movement in the real space of an image pickup part of a detected body;

a step for making a correction different from that of a second area in a first area of image data of the image pickup part of the detected body collected by a scan of magnetic resonance imaging on the basis of the movement information; and a step for synthesizing the respective corrected image data of the first area and the second area.

To achieve the above object, an image data correcting method in the present invention also comprises:

a step for making a correction different from that of a second area in a first area of image data of an image pickup part of a detected body collected by a scan of magnetic resonance imaging on the basis of movement information showing a spatial distribution of the magnitude of a movement in the real space of the image pickup part; and a step for synthesizing the respective corrected image data of the first area and the second area.

To achieve the above object, an image data correcting method in the present invention also comprises:

a step for converting data of a first space in a first area and a second area of an image pickup part of a detected body into data of a second space in a third area and a fourth area;

a step for making a correction different from that of the fourth area with respect to the data of the second space in the third area;

a step for synthesizing the data of the second space in the third area after the correction, and the data of the second space in the fourth area; and a step for converting the data of the second space after the synthesis into data of the first space.

To achieve the above object, an image data correcting method in the present invention also comprises:

a step for converting data of at least one area among data of a first space of plural areas in an image pickup part of a detected body into data of a second space;

a step for correcting the data of the second space; and a step for converting the data of the second space after the correction into data of the first space.

To achieve the above object, a magnetic resonance imaging device in the present invention comprises:

a movement information acquiring section for acquiring movement information showing a spatial distribution of the magnitude of a movement in the real space of an image pickup part of a detected body;

an image data collecting section for collecting image data of the image pickup part of the detected body by a scan of magnetic resonance imaging;

a correcting section for making a correction different from that of a second area in a first area of the collected image data on the basis of the movement information; and a synthesizing section for synthesizing the respective image data of the first area and the second area corrected by the correcting section.

To achieve the above object, a magnetic resonance imaging device in the present invention also comprises:

an image data collecting section for collecting image data of an image pickup part of a detected body by a scan of magnetic resonance imaging;

a correcting section for making a correction different from that of a second area in a first area of the collected image data on the basis of movement information showing a spatial distribution of the magnitude of a movement in the real space of the image pickup part; and a synthesizing section for synthesizing the respective image data of the first area and the second area corrected by the correcting section.

To achieve the above object, a magnetic resonance imaging device in the present invention also comprises:

a data collecting section for collecting data of a first space in an image pickup part of a detected body by a scan of magnetic resonance imaging;

a first data converting section for converting the data of the first space in a first area and a second area into data of a second space in a third area and a fourth area;

a correcting section for making a correction different from that of the fourth area with respect to the data of the second space in the third area;

a synthesizing section for synthesizing the data of the second space in the third area after the correction, and the data of the second space in the fourth area; and a second converting section for converting the data of the second space after the synthesis into data of the first space.

To achieve the above object, a magnetic resonance imaging device in the present invention also comprises:

a data collecting section for collecting data of a first space in an image pickup part of a detected body by a scan of magnetic resonance imaging;

a first data converting section for converting data of at least one area among the data of the first space of plural areas into data of a second space;

a correcting section for correcting the data of the second space; and a second data converting section for converting the data of the second space after the correction into data of the first space.

In accordance with such magnetic resonance imaging devices, image data correcting devices and image data correcting methods in the present invention, when the image is obtained from data of the k-space particularly collected and filled by using the pulse sequence of the multi-shot type in the magnetic resonance imaging, echo data spatially ununiformly deteriorated and collected by the nonlinear movement of the image pickup part at high speed are corrected as a sum (synthesis) of data linearly corrected in accordance with a moving degree. Thus, an MR image comparatively simply corrected at high speed is obtained.

BRIEF DESCRIPTION OF THE DRAWINGS

FIG. 18 is a view showing a fault image obtained by dividing and correcting the k-space data by using the single coil and including an air portion in software by the present invention when there is a movement of the non-rigid body having the one-dimensional distribution in the PE direction.

FIG. 19 is a view showing a fault image in which k-space data divided into two portions in hardware by using the multi-coil having two element coils by the present invention are further divided into two portions in software by using the window function, and the fault image is obtained by linearly correcting the k-space data equivalently divided into three portions when there is a movement of the non-rigid body having the one-dimensional distribution in the PE direction.

BEST MODE FOR CARRYING OUT THE INVENTION

The embodiment modes of the present invention will next be explained with reference to the drawings.

First Embodiment Mode

One embodiment mode in accordance with a magnetic resonance imaging device of the present invention will next be explained with reference to FIGS. 1 to 5.

Figure 1:
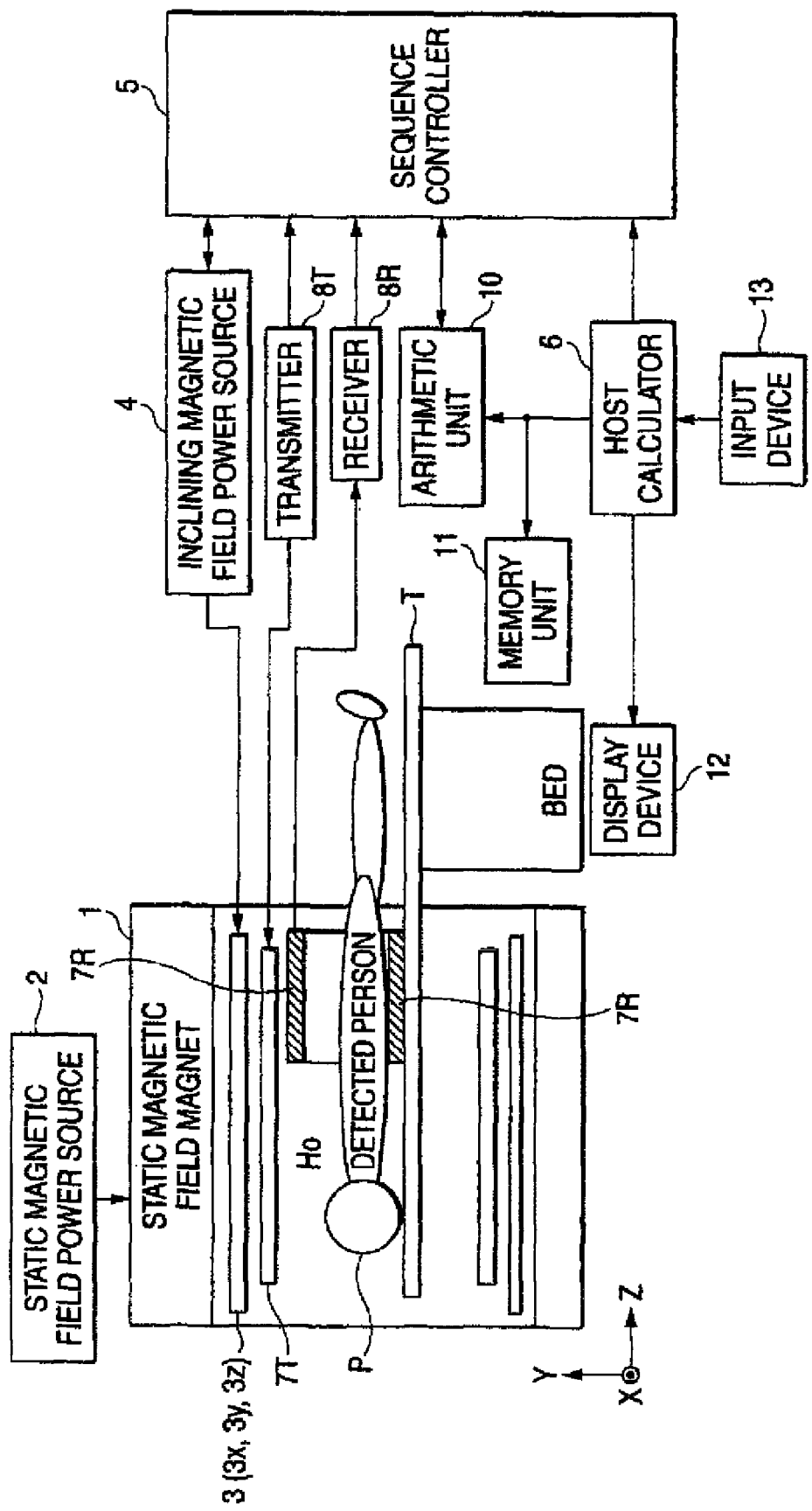
FIG. 1 is a block diagram showing one embodiment mode of a magnetic resonance imaging device in the present invention and relating to a construction.

FIG. 1 shows the schematic construction of the magnetic resonance imaging (MRI) device in this embodiment mode.

This magnetic resonance imaging device has a bed section for arranging a detected body P thereon, a static magnetic field generating section for generating a static magnetic field, an inclining magnetic field generating section for adding position information to the static magnetic field, a signal transmitting-receiving section for transmitting and receiving a high frequency signal, and a control-arithmetic section for being in charge of the control of an entire system and the reconstruction of an image.

For example, the static magnetic field generating section has a magnet 1 of a superconducting system, and a static magnetic field power source 2 for supplying an electric current to this magnet 1. A static magnetic field $H_0$ is generated in the axial direction (Z-axis direction) of a cylindrical opening portion (a space for diagnosis) into which the detected body P is inserted with play. An unillustrated shim coil is arranged in this magnet section. In the bed section, a roof plate T arranging the detected body P thereon can be inserted into the opening portion of the magnet 1 so as to be escaped.

The inclining magnetic field generating section has an inclining magnetic field coil unit 3 assembled into the magnet 1. This inclining magnetic field coil unit 3 has three sets (kinds) of x, y and z coils 3x to 3z for generating the inclining magnetic fields of the X-axis direction, the Y-axis direction and the Z-axis direction perpendicular to each other. The inclining magnetic field section also has an inclining magnetic field power source 4 for supplying electric currents to the x, y and z coils 3x to 3z. This inclining magnetic field power source 4 supplies pulse electric currents for generating the inclining magnetic fields to the x, y and z coils 3x to 3z under the control of a sequencer 5 described later.

The inclining magnetic fields of the directions of the three axes (the X-axis, the Y-axis and the Z-axis) as physical axes are synthesized by controlling the pulse electric currents supplied from the inclining magnetic field power source 4 to the x, y and z coils 3x to 3z. It is then possible to arbitrarily set and change logic axis directions constructed by a slice direction inclining magnetic field $G_S$, a phase encode direction inclining magnetic field $G_E$ and a read-out direction (frequency encode direction) inclining magnetic field $G_R$ perpendicular to each other. The respective inclining magnetic fields of the slice direction, the phase encode direction and the read-out direction are superposed onto the static magnetic field $H_0$.

The signal transmitting-receiving section has a signal transmitting RF (high frequency) coil 7T and a signal receiving RF coil 7R arranged in the vicinity of the detected body P in a photographing space within the magnet 1, and also has a signal transmitter 8T and a signal receiver 8R respectively connected to these RE coils 7T and 7R.

The signal receiving RF coil 7R is a single coil as one coil element, or is a multi-coil constructed by plural coil elements, and each coil is formed as a surface coil. The signal receiving RF coil is arranged along the body surface of an abdominal part, etc. as an image pickup part of the detected body P (tested person). For example, the signal transmitting RE coil is formed as a coil for the whole body.

The signal transmitter 8T and the signal receiver 8R are operated under the control of the sequencer 5 described later. The signal transmitter 8T supplies an RF (radio frequency) electric current pulse of a Larmor frequency for exciting nuclear magnetic resonance (NMR) to the signal transmitting RE coil 7T by these operations. The signal receiver 8R fetches a magnetic resonance (MR) signal (high frequency signal) received by the signal receiving RE coil 7R. The signal receiver 8R then performs various kinds of signal processings such as pre-amplification, intermediate frequency conversion, phase wave detection, low frequency amplification, filtering, etc. with respect to this MR signal. Thereafter, the signal receiver 8R performs A/D conversion, and generates digital data (original data) of the MR signal.

The control-arithmetic section has the sequencer (also called a sequence controller) 5, a host computer 6, an arithmetic unit 10, a memory unit 11, a display device 12 and an input device 13. The host computer 6 has a function for giving a command of pulse sequence information to the sequencer 5 by an unillustrated stored software procedure, and generalizing the operation of the entire device.

As a pulse sequence used in a scan, a pulse series of a two-dimensional or three-dimensional multi-shot type using a high speed SE (spin echo) method, a high speed FE (field echo) method, an EPI (echo planar imaging) method, a FASE (fast asymmetric (advanced) spin echo) method, a GRASE (gradient and spin echo) method, etc. is used. Data are divided on the basis of information of the r-space even when the correction is executed in the k-space. Therefore, the k-space may be sampled in any method. Therefore, such a pulse series may be concretely a pulse series based on any one of the spin warp method, the spiral method and the radial method. Thus, when the artifact is localized near a generating source by the correction described later, a large correction effect is particularly shown. In the case of the magnetic resonance imaging in which no movement between generated echoes can be neglected, the correction in the present invention can be applied even in the scan of a single shot type.

The sequencer 5 has a CPU (Central Processing Unit) and a memory. The sequencer 5 stores pulse sequence information sent from the host computer 6J and controls the operations of the inclining magnetic field power source 4, the signal transmitter 8T and the signal receiver 8R in accordance with this information. Further, the sequencer 5 is constructed such that digital data of a magnetic resonance signal outputted by the signal receiver 8R are once inputted to the sequencer 5, and these digital data are transferred to the arithmetic unit 10. Here, the pulse sequence information is all information required to operate the inclining magnetic field power source 4, the signal transmitter 8T and the signal receiver 8R in accordance with a series of pulse sequences. For example, this pulse sequence information includes information relative to the intensities of pulse electric currents applied to the x, y and z coils $3x$ to $3z$, application times, application timing, etc.

The digital data (also called original data or raw data) outputted by the signal receiver 8R are inputted to the arithmetic unit 10 through the sequencer 5, and are arranged in the k-space (also called a Fourier space or a frequency space) using its internal memory. These data are reconstructed to image data of the real space by performing the two-dimensional or three-dimensional Fourier transform every one set.

The arithmetic unit 10 is also set to be able to execute correction processing in the present invention in accordance with a predetermined algorithm. This correction processing is processing for correcting spatially uniform (nonlinear) deterioration due to a movement of the detected body with respect to the image data reconstructed at the present time point or already acquired as after-treatment. For example, when an image of the abdominal part of the detected body P is picked up, each sampling position of this abdominal part is spatially nonlinearly moved by the movement (body movement) of a breathing property. Thus, the acquired image data are spatially ununiformly deteriorated. Since this is matters forming a central portion of the present invention, these matters will be described later in detail.

The arithmetic unit 10 can also execute synthesis processing and differential arithmetic processing of data relative to an image in accordance with necessity. This synthesis processing includes processing for making an adding calculation every pixel, maximum value projection (MIP: Maximum Intensity Projection) processing, etc.

The memory unit 11 can store image data performed with respect to the above synthesis processing and differential processing as well as the reconstructed image data. For example, the display device 12 is used to display the reconstructed image. Further, parameter information desired by an operator, information relative to a scan condition, the pulse sequence, the image synthesis and the differential arithmetic calculation, etc. can be inputted to the host computer 6 through the input device 13.

Here, the correction processing as after-treatment performed with respect to the above image data will be explained.

(Nature of Nonlinear Movement)

In the spatial movement of a living body as the detected body, there are the linear movement and the nonlinear movement as already described. "The spatial nonlinear movement" means that there is a spatial distribution in the amplitude and phase of this movement. With respect to a periodic property, there are many cases in which the movement due to the breathing property and a heartbeat, etc. is periodic. However, a sudden unexpected movement (involuntary motion) is non-periodic.

When the images of internal organs of the abdominal part are formed, each sampling position of an image pickup area of the abdominal part is strongly influenced by the movement (body movement) of the breathing property. This movement of the breathing property spatially becomes nonlinear (ununiform). Therefore, in this embodiment mode, when the internal organs of the abdominal part, etc. are diagnosed, an echo signal mixed with a movement component spatially ununiformly distributed by such a nonlinear movement of the breathing property is collected. A spatially ununiformly deteriorated signal component of this echo signal is corrected.

The movement can be also classified into rigid body deformation causing only parallel translation and rotation, and non-rigid body deformation causing linear deformation and nonlinear deformation including enlargement and reduction and shearing. In accordance with the present invention, more accurately, the correction can be effectively made with respect to the echo signal into which the movement component spatially ununiformly distributed by the movement of the nor-rigid body deformation is mixed. Accordingly, data deteriorated by the linear deformation among the nonrigid body deformation are set to an object, and the correction can be also made. However, in the following description, an explanation will be made with the correction about the nonlinear deformation as an object.

Figure 2:
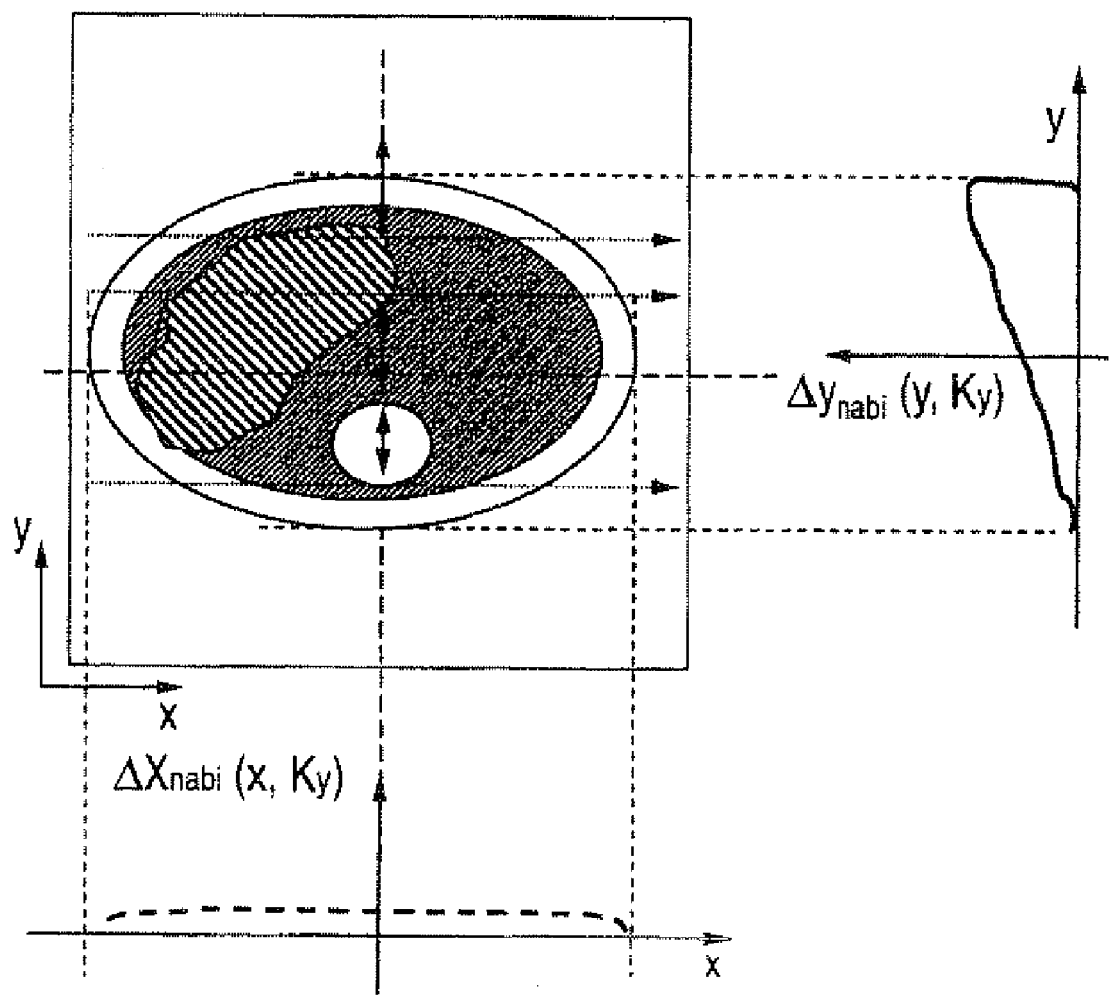
FIG. 2 is a view for explaining a section of the abdominal part of a detected body and a movement of each part thereof.

A certain model with respect to the movement of the living body is supposed to make this correction (see FIG. 2). In this model, an axial section image of the abdominal part is set to an object as a sectional image showing the spatially nonlinear movement most preferably, but may not be necessarily set.

In the axial section image of the abdominal part, as in the model shown in FIG. 2, it can be supposed that the amplitude of the movement of the breathing property can be neglected on the back side, but becomes largest on its opposite abdominal wall side (front side), and the amplitude therebetween is gradually increased from the back side to the abdominal wall side. It is now supposed that the amplitude of the movement of a certain two-dimensional object body is uniform in the x-direction and is increased from the back side to the abdominal wall side in the y-direction in proportion to its distance y. When it is considered that the axial section shape of the abdominal part is approximately elliptical and the contrast is approximately symmetrical on the front, rear, left-hand and right-hand sides, it is considered that an average shift amount of the entire image acquired in certain timing reflects the movement of the central portion of a photographed body. At this time, it can be considered that the amplitude of the movement in the y-direction becomes zero at the back side end, and becomes maximum and shows a change twice that of the central portion at the side end of the abdominal wall.

Therefore, the following technique is adopted in this embodiment mode. Namely, the k-space is divided by using information of the nonlinear movement measured or estimated in the r-space, i.e., the magnitude (order) of this movement. Phase corrections of a zeroth order different from each other are made in these plural divided k-spaces. These corrected data are mutually weighted and added.

(Detection of Nonlinear Movement and its Correction)

Figure 3:
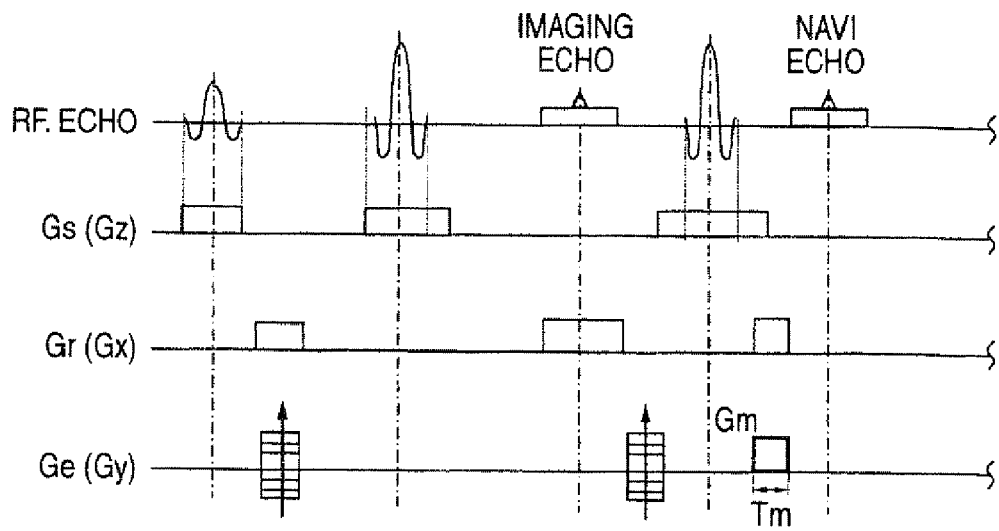
FIG. 3 is a view showing one portion of a pulse sequence using a navigator usable in the embodiment mode of the present invention.
Figure 4:
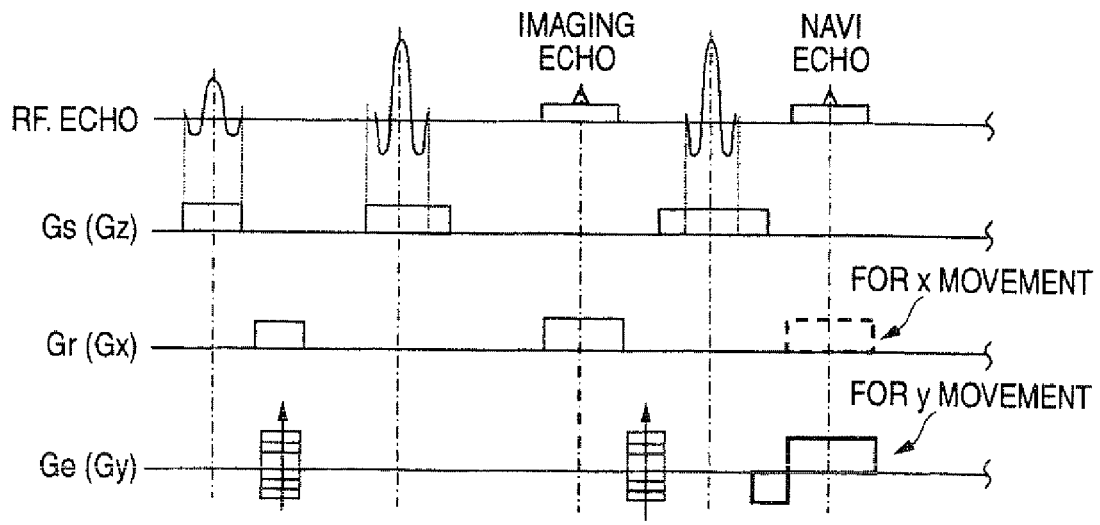
FIG. 4 is a view showing one portion of another pulse sequence using the navigator usable in the embodiment mode of the present invention.
Figure 5:
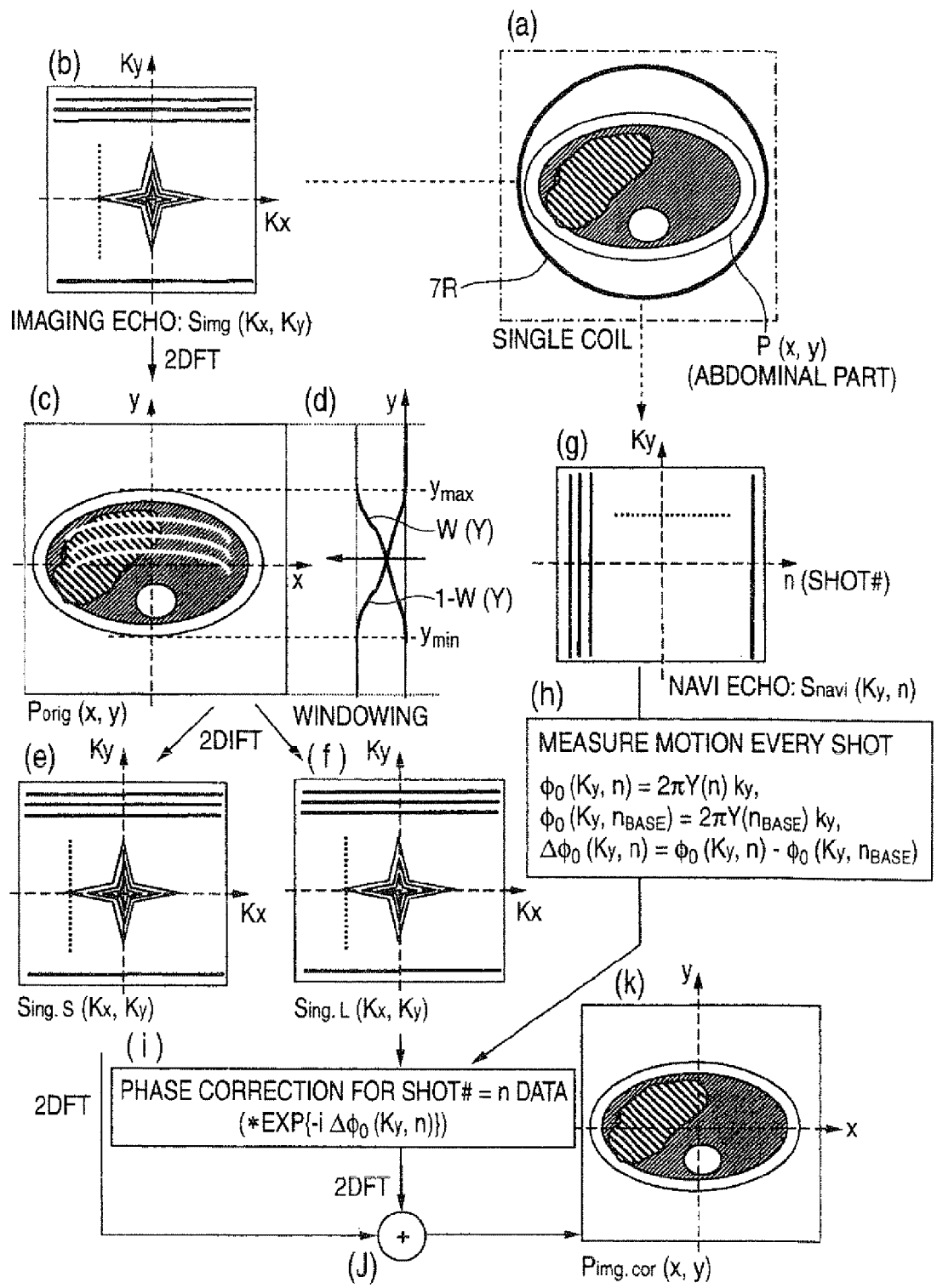
FIG. 5 is a view for schematically explaining data collection, a nonlinear correction and the procedure of a reconstruction in accordance with a first embodiment mode.

Next, a concrete technique of the detection of the above nonlinear movement and its correction will be explained. FIGS. 3 to 5 schematically show such a technique.

It is now supposed that the image pickup part is the abdominal part of the detected body, and a surface coil constructed by the single coil is arranged as the RF signal receiving coil 7R around this abdominal part (see FIG. 5(a)).

As mentioned above, each position of the abdominal part is spatially nonlinearly moved in accordance with a breath. Accordingly, when the abdominal part is diagnosed, it is necessary to spatially perform division and processing in accordance with the largeness or smallness of the movement. On the other hand, since it is desirous to execute the phase correction in the k-space from convenience of the processing, it is desirous to divide data filled in the k-space dependently on the magnitude of the spatial movement.

In the data filled in the k-space, position information relative to the distribution of the movement is already equally scattered. Accordingly, it is difficult to perform the division using the spatial information of the k-space itself.

Therefore, a method for dividing data of the r-space by using the spatial distribution information of the movement is adopted. Here, the axial section of the abdominal part is set to an object. a) The knowledge (presumption) of "the abdominal side is larger than the back side" is used as an index of the distribution in the monitor of a zeroth order phase and the space dependency of the movement. Otherwise, b) the forward-backward direction (direction directed from the back side to the abdominal wall direction) of the detected body is actually set to the phase encode direction, and a method for monitoring the movement of the abdominal part of this direction by a navigator echo (hereinafter called a navi echo) responsive to an inclining magnetic field pulse for navigation, etc. is adopted.

The shift of the average (zeroth order) phase in the r-space becomes a phase shift of a first order in the k-space. Further, the shift of the position in the r-space becomes a phase shift of the first order in the k-space.

Accordingly, when a phase error is $\exp(i\phi_0)$, the product of each pixel data and $\exp(-i\phi_0)$ is arithmetically calculated uniformly in both the r-space and the k-space to correct its phase. Further, if the shift distance in the r-space is $\Delta Y$ in the y-direction, the product with respect to $\exp[-2\pi K_y \Delta Y]$ is arithmetically calculated in the k-space.

When a method for monitoring only the average amplitude of the movement described in the above item a) and linearly externally mounting and correcting an amplitude change of the movement in the phase encode direction is adopted, it is preferable to use a pulse sequence to which an inclining magnetic field causing the phase shift of a constant value in the phase encode direction in the navi echo is applied. FIG. 3 shows an example of this pulse sequence.

When the projection data of the phase encode direction described in the above b) item are collected, a similar inclining magnetic field is applied in both the phase encode direction and the read-out direction before the navi echo is collected. FIG. 4 shows this example.

Each of FIGS. 3 and 4 shows a pulse series based on the high speed SE method to which the spin warp method is applied as the pulse sequence. However, only one echo with respect to one shot is illustrated from the relation of the paper face.

The echo signal is collected by using such a pulse sequence shown in FIG. 3 or 4, and its echo data are arranged in the two-dimensional k-space (see FIG. 5(b)). These echo data are reconstructed to image data of the real space performed with respect to the two-dimensional Fourier transform (DEFT) by the arithmetic unit 10 (see FIG. 5(c)).

Here, when the data distribution of the k-space is divided in accordance with the spatial movement of the abdominal part, an example for most simply dividing the k-space into two portions in its phase encode direction is shown. In this case, the image of the real space is multiplied by a window in the y-axis direction corresponding to the phase encode direction (more particularly, the image is multiplied by a window function). The image is then divided into respective two dominant areas in a moving degree in data on the abdominal wall side (the front side of the abdominal part) and the back side (the rear side of the abdominal part) (see FIGS. 5(c) and 5(d)). The two real spaces divided in these data are respectively transformed to two two-dimensional k-spaces by two-dimensional inverse Fourier transform (2DIFT) (see FIGS. 5(e) and 5(f)).

On the other hand, the navi echo $S_{navi}(K_y,n)$ is collected every shot by executing the above pulse sequence (see FIG. 5(g)). Accordingly, the phase error $\Delta\phi_0(K_y,n)$ as movement information of the abdominal part is measured from this navi echo $S_{navi}(K_y,n)$ (see FIG. 5(h)).

This measurement is concretely executed every shot n as the following formulas.

$$\phi_0(K_y,n)=2\pi Y(n)K_y$$

$$\phi_0(K_y,n_{base})=2\pi Y(n_{base})K_y$$

$$\Delta\phi_0(K_y,n)=\phi_0(K_y,n)(K_y,n_{base}) \quad \text{[Formula 1]}$$

Here, Y(n) is a shift amount of the movement in the shot n.

Next, the phase correction is made with respect to only data of the k-space having data of the abdominal wall side (see FIG. 5(i)). No phase correction is made with respect to data of the k-space having data of the back side. Such a phase correction is made by multiplying data of each shot every shot n by the following formula.

$$\exp[-i\Delta\phi_0(K_y,n)] \quad \text{[Formula 2]}$$

The two-dimensional Fourier transform (2DFT) is performed with respect to each of these two k-spaces, and it is returned to the individual real spatial data. A pixel value is mutually added and the final real spatial data are obtained (see FIGS. 5(j) and 5(k)).

Here, the collection of the above echo data (including data of the navi echo) and the correction processing will be explained by forming numerical formulas. In this embodiment mode, this processing is executed by the arithmetic unit 10, but one portion of this processing may be also entrusted to the host computer 6.

Here, the following symbols are set.
[Formula 3]
$S_{img}(x,y)$: echo data of an imaging object,
$S_{navi}(x,Ky)$: navi echo of the x-axis (read-out) direction performed with respect to one-dimensional Fourier transform (FT),
$Ax_{navi}(x,n)$: amplitude of movement of the x-axis direction sampled in n-th shot
$Ay_{navi}(x,n)$: amplitude of movement of the y-axis direction sampled in n-th shot
$\phi x_{navi}(Kx,n)$: phase of navi echo of the x-axis direction sampled in n-th shot
$\phi y_{navi}(Ky,n)$: phase of navi echo of the y-axis direction sampled in n-th shot
$W_{L,M,S}(y)$: window function for selecting a control area of movement in a human body
n: shot number ($1=1-N_{max}$)

First, echo data are collected by using the pulse sequence based on the FSE method using the normal spin warn method as simplest one echo/shot of the multi-shot type shown in the above FIG. 3 or 4, and its image data are obtained (processing 1). Namely, when echo data $S_{img}(Kx,Ky)$ are set, image data $P_{img}(x,y)$ of its real space are obtained as the following formula.

$$P_{img}(x,y)=FT2D_{Kx \to x, Ky \to y}[S_{img}(Kx,Ky)] \quad \text{Formula [4]}$$

At this time, navi echo $S_{navi}(K_y,n)$ is also simultaneously collected.

Next, the arithmetic unit 10 selects a spatial area in accordance with the order (magnitude) of the movement. Namely, a window for dividing the area of the k-space is determined (processing 2).

Concretely, both edge positions $y_{min}$ and $y_{max}$ of the abdominal part of the detected body in the phase encode direction are first detected. If the navi echo is collected and the profile of a one-dimensional movement is measured and is used, an index $\Delta Y(y)$ of the spatial distribution of the movement is arithmetically calculated. Thus, the profile W(y) of the y-axis direction, i.e., the phase encode direction is obtained as the following formula.

$$W(y)=\Delta Y(y)/\{\Delta y_{max}-\Delta y_{min}\} \quad \text{[Formula 5]}$$

(or $\Delta Y$ may be replaced with phase $\phi$)

If necessary, this profile W(y) may be also smoothed and set to the profile W(y).

Accordingly, for example, when the k-space data are divided into two portions in the phase encode direction (here the y-axis direction: see FIG. 2), the window function $W_{L,M,S}(y)$ for performing these two divisions becomes the following formulas.

$$W_L(y)=W(y)$$

$$W_S(y)=1-W_L(y) \quad \text{[Formula 6]}$$

If the k-space data are divided into three portions (see FIG. 6), the window function $W_{L,M,S}(y)$ becomes the following formulas.

$$W_L(y) = 2 \cdot \max[W(y) - 0.5, 0] \quad \text{[Formula 7]}$$

$$W_M(y) = \{1 - W_L(y)\} \text{ (when } W(y) >= 0.5)$$

$$= W(y) \text{ (otherwise)}$$

$$W_S(y) = 1 - W_L(y) - W_M(y)$$

Figure 6:
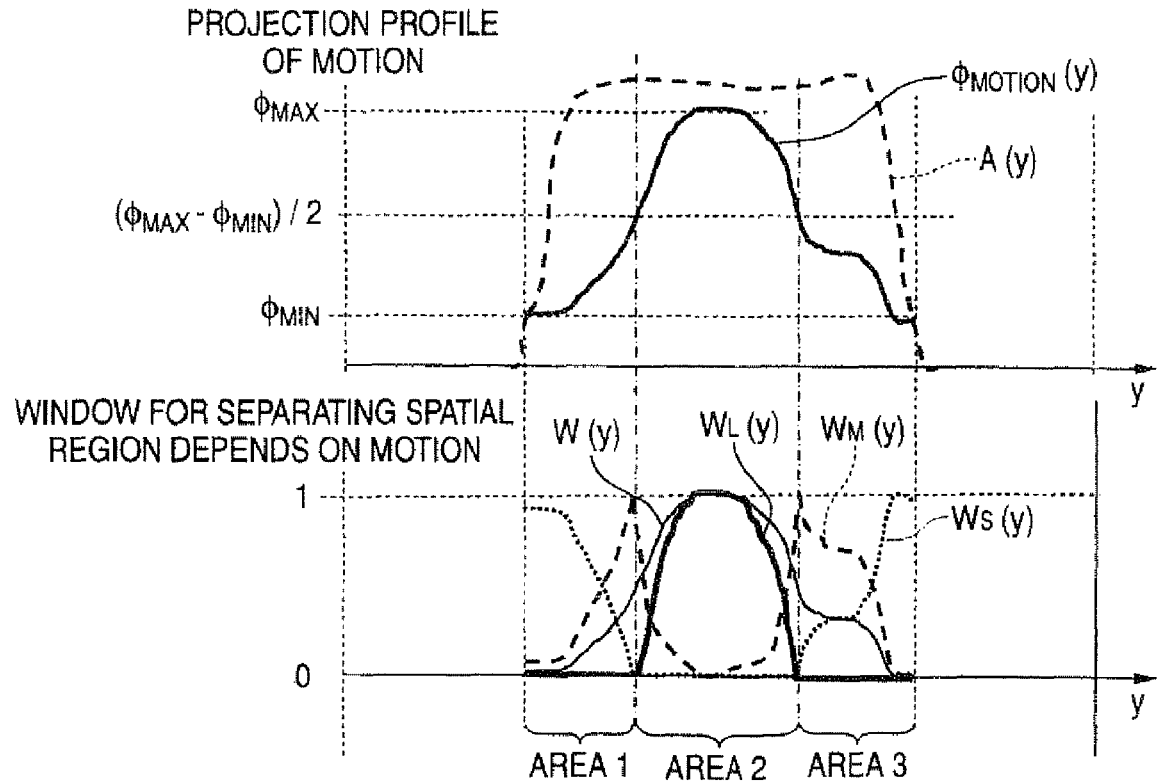
FIG. 6 is a graph showing an example of a window function W made when data of an area of the k-space are divided into three portions.

FIG. 6 explains setting of the window function $W_{L,M,S}(y)$ when the k-space data are divided into three portions. In this figure, as an index showing the movement distribution in the y-direction of the r-space, its ordinate axis is shown by phase $\phi$. This ordinate axis may be also shown by the position shift $\Delta Y$.

Next, when the k-space is divided into three portions, the arithmetic unit 10 respectively divides the data of the k-space into data $S_L(K_x,K_y)$, $S_M(K_x,K_y)$ and $S_S(K_x,K_y)$ of a larger area, a medium area and a smaller area of the movement by using the calculated window function $W_{L,M,S}(y)$ and the image data $P_{img}(x,y)$ of the real space. Namely, the data of the k-space are divided into data of plural areas (processing 3). In this case, the following arithmetic calculations are made.

$$P_L(x,y)=W_L(y)P_{img}(x,y) \quad \text{[Formula 8]}$$

(with respect to image data of the larger area of movement)

$$P_M(x,y)=W_M(y)P_{img}(x,y)$$

(with respect to image data of the medium area of movement)

$$P_S(x, y) = W_S(y)P_{img}(x, y)$$

$$= P_{img}(x, y) - P_L(x, y) - P_M(x, y)$$

(with respect to image data of the smaller area of movement)

$$S_L(K_x,K_y)=IFT_{x \to Kx, y \to Ky}[P_L(x,y)]$$

$$S_M(K_x,K_y)=IFT_{x \to Kx, y \to Ky}[P_M(x,y)]$$

$$S_S(K_x,K_y)=IFT_{x \to Kx, y \to Ky}[P_S(x,y)]$$

$$=S(K_x,K_y)-S_L(K_x,K_y)-S_M(K_x,K_y)$$

Next, the following processings 4 to 6 are sequentially repeatedly executed by the arithmetic unit 10 every shot n, i.e., until shot n=1 to $N_{max}$.

First, the phase distribution in the k-space $\phi(Ky,n)$ caused by the movement is calculated from the navi echo $S_{navi}(Ky,n)$ (processing 4).

$$P_{navi}(y,n)=FT_{Ky \to y}[S_{navi}(K_y,n)]$$

$$\Delta Y(y,n)=Y(y,n)-Y(y,n_{base})$$

$$\Delta Y_{mean}(n)=\int \Delta(y,n)dy$$

$$\Delta Y_{max}(n)=\text{max of } [\Delta Y(y,n)] \quad \text{[Formula 9]}$$

Here, the echo data of a base are selected on the basis of central data ($n=N_{max}/2$) of the k-space or an average of all $\Delta Y(y,n)$.

Next, a maximum value $\phi_{max}(K_y,n)$ of the phase distribution in the k-space is arithmetically calculated (processing 5). Concretely, when a linear model and a zero order phase are used, the following formulas are formed.

$$\Delta \phi_0(K_y,n)=2\pi K_y \Delta Y_{mean}(n)$$

$$\Delta \phi_{max}(K_y,n)=2 \cdot \text{max of } [\Delta \phi_0(K_y,n)] \quad \text{[Formula 10]}$$

When the profile $\Delta Y(y,n)$ of one-dimensional projection of the y-axis direction is used, the following formula is formed.

$$\Delta \phi_{max}(K_y,n)=2\pi K_y \Delta Y_{max}(y,n) \quad \text{[Formula 11]}$$

Next, the phase correction is made with respect to $K_y$ in the same shot (processing 6). Concretely, the following formulas are formed.

$$S_{L.cor}(K_x,K_y)=S_L(K_x,K_y)\exp[-i\Delta \phi_{max}(K_y,n)]$$

$$S_{M.cor}(K_x,K_y)=S_M(K_x,K_y)\exp[-i\Delta \phi_{max}(K_y,n)/2] \quad \text{[Formula 12]}$$

Thus, the loop every shot n is terminated.

Next, the arithmetic unit 10 synthesizes all the divided data of the k-space by the following formula (processing 7).

$$S_{img.cor}(K_x,K_y)=S_{L.cor}(K_x,K_y)+S_{M.cor}(K_x,K_y)+S_S(K_x,K_y) \quad \text{[Formula 13]}$$

The correction data $S_{img.cor}(K_x,K_y)$ of the entire k-space calculated in this way are reconstructed to image data of the real space by the two-dimensional Fourier transform (processing 8). If this reconstruction is formed by a formula, this formula is provided as follows.

$$P_{img.cor}(x,y)=FT2D_{Kx \to x, Ky \to y}[S_{img.cor}(K_x,K_y)] \quad \text{[Formula 14]}$$

Thus, in accordance with this embodiment mode, the k-space data are divided in consideration of a moving degree by using information of the movement of the abdominal part measured or estimated in the r-space. Further, linear movement corrections different from each other according to such a moving degree are executed every divided data. The corrected divided data are finally synthesized. Here, the linear correction includes all corrections defined by affine transformation.

Namely, with respect to data deteriorated by the nonlinear movement of an image pickup part in which a large amount of complicated and arithmetic calculations are conventionally required and it is substantially difficult to execute these calculations, a nonlinear data correction is realized in substitution by dividing the image data in accordance with the moving degree, and making the linear moving correction with respect to each divided data, and synthesizing the divided data after this correction.

Even when MR imaging of the multi-shot type is performed by this substituting nonlinear correction, the phase of the data spatially deteriorated by the spatial nonlinear movement of the abdominal part, etc. can be easily corrected at high speed. As this result, the artifact caused by generating the spatial ununiform nonlinear position shift and phase shift by an influence of such a nonlinear movement can be simply corrected at high speed, and image quality can be improved.

Here, an explanation of the above pulse sequence of FIG. 3 will be supplemented. This pulse sequence is a sequence provided when only a zeroth order (average) phase shift is measured in the r-space provided by the movement along the phase encode direction of imaging every shot # in the navi echo. An inclining magnetic field (navigator) of intensity $G_m$ and time $T_m$ is applied in the phase encode direction Ge before the navi echo $S_{navi}(K_y,n)$, and an average phase (corresponding to a central phase in the k-space) in the r-space is measured, and a difference with respect to a base shot is calculated.

$$\phi_{navi0}(n)=arg[S_{navi}(K_y=0,n)]$$

$$\Delta \phi_{navi0}(y,n)=\phi_{navi0}(n)-\phi_{navi0}(n_{base}) \quad \text{[Formula 15]}$$

It can be also converted into an average shift amount $\Delta Y_0(n)$ in the r-space by using the relation of $\phi_{navi0}(n)=(2\pi G_m T_m)\Delta Y_0(n)$. Further, A/D sampling with respect to the navi echo $S_{navi}(K_y,n)$ may be narrowly set since it is sufficient to be able to measure only the phase of the center (DC) of the k-space.

In a pulse series portion for the navi echo, the FE method able to shorten time may be also used instead of the SE method if a signal can be sufficiently secured. This is because susceptibility effects caused by the FE method and the phase shift originated from the static magnetic field are canceled since the difference with respect to the echo using the base shot is calculated.

Second Embodiment Mode

Next, one embodiment mode in accordance with the magnetic resonance imaging device of the present invention will be explained with reference to FIGS. 1 and 7. The hardware construction of the magnetic resonance imaging device in this embodiment mode is the same as the above hardware construction described in FIG. 1, and its explanation is therefore omitted.

In this embodiment mode, a multi-coil is used in the signal receiving RF coil 7R in hardware, and an efficient correction is realized by linking data collection utilizing respective sensitivity areas of two coil elements forming this multi-coil, and correction processing of the present application invention. When a case for picking-up the image of the abdominal part is particularly considered and a ghost (a nonlinear component caused by the movement) from the abdominal wall side is extended onto the back side, the ghost is included in data of the lung side. In this case, even when the supposition of FIG. 2 with respect to the movement is correct, the fear of whether its influence can be finally neglected is left. In this embodiment mode, such a fear can be reliably wiped out.

Figure 7:
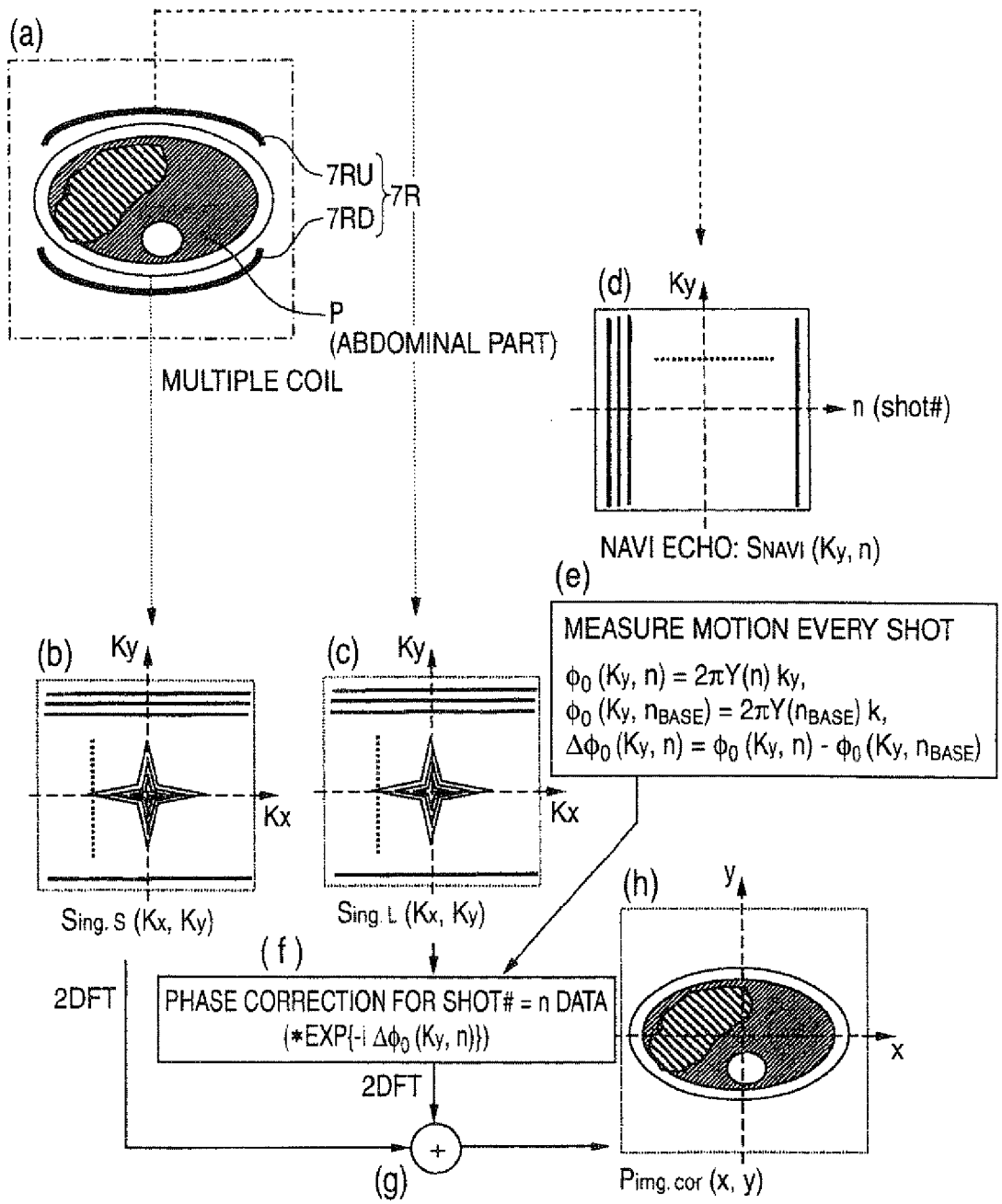
FIG. 7 is a view for schematically explaining data collection, a nonlinear correction and the procedure of a reconstruction in accordance with a second embodiment mode.

As shown in FIG. 7(*a*), in this multi-coil 7R as the signal receiving RF coil, two surface coils 7RU, 7RD respectively arranged oppositely on the back side and the abdominal wall side of the abdominal part are set to element coils. A pickup image provided by combining such a multi-coil and a dedicated image reconstruction is widely practically used in recent magnetic resonance imaging to shorten image pickup time and improve SNR (signal to noise ratio). When the image of the abdominal part is picked up, there are many cases in which two surface coils are arranged on the back side and the abdominal wall side as shown in FIG. 7(*a*).

One surface coil 7RU of the abdominal wall side has stronger detecting sensitivity on this abdominal wall side by arranging the surface coils 7RU, 7RD in this way. Therefore, a large weight is applied to the abdominal wall side with respect to a signal from the surface coil 7RU, and the movement of this abdominal wall side is detected as a dominant component. The other surface coil 7RD of the back side has stronger detecting sensitivity on this back side. Therefore, a component small in the movement of the back side is dominantly detected in a signal from this surface coil 7RD. Namely, two sets of k-space data divided by reflecting the nonlinear moving degree of the abdominal part can be preferably respectively collected from the beginning by respectively arranging these two surface coils 7RU, 7RL along the abdominal wall side and the back side of the abdominal part (see FIGS. 7(b), 7(c)).

These two sets of k-space data respectively correspond to FIGS. 5(e), 5(f) in the above first embodiment mode. Accordingly, the Fourier transform and the window processing corresponding to FIGS. 5(c), 5(d) are not required. The processings of FIGS. 7(d) to 7(h) are the same as the above processings of FIGS. 7(g) to 7(k).

The echo data spatially differently weighted can be directly collected from the abdominal part of the detected body P by the two surface coils 7RU, 7RD arranged in this way. In particular, there are many cases in which the surface coils are conventionally arranged on the abdominal wall side and the back side in the signal receiving RF coil in the diagnosing case of the abdominal part. Therefore, the echo data dominantly influenced by a large movement of the abdominal wall side from the two surface coils 7RU, 7RD, and the echo data dominantly influenced by a small movement of the back side are collected from the beginning.

Therefore, the above correction processing is performed with respect to only the echo data from the abdominal wall side, and the respective k-space data are reconstructed and are mutually added. Thus, final image data $P_{img\_cor}(x,y)$ of the real space can be obtained (see FIGS. 7(d) to 7(h)).

Accordingly, in accordance with this second embodiment mode, differing from the above first embodiment mode, even when the ghost is extended by the movement of the abdominal wall side until the back side, a generating source signal of the ghost is preponderantly included in only the echo data from the surface coil 7RU of the abdominal wall side. Namely, the influence of the ghost included in the echo data from the surface coil 7RD of the opposite side is restrained from the beginning. Therefore, if the echo data from the surface coil 7RU of the abdominal wall side are corrected as they are, it becomes equivalent to the correction including the ghost extended to the back side far from the abdominal wall side. Accordingly, in comparison with the case of the single coil adopted in the first embodiment mode, it is possible to finally obtain the reconstructing image of image quality further improved in processing time and correction precision.

Figure 8:
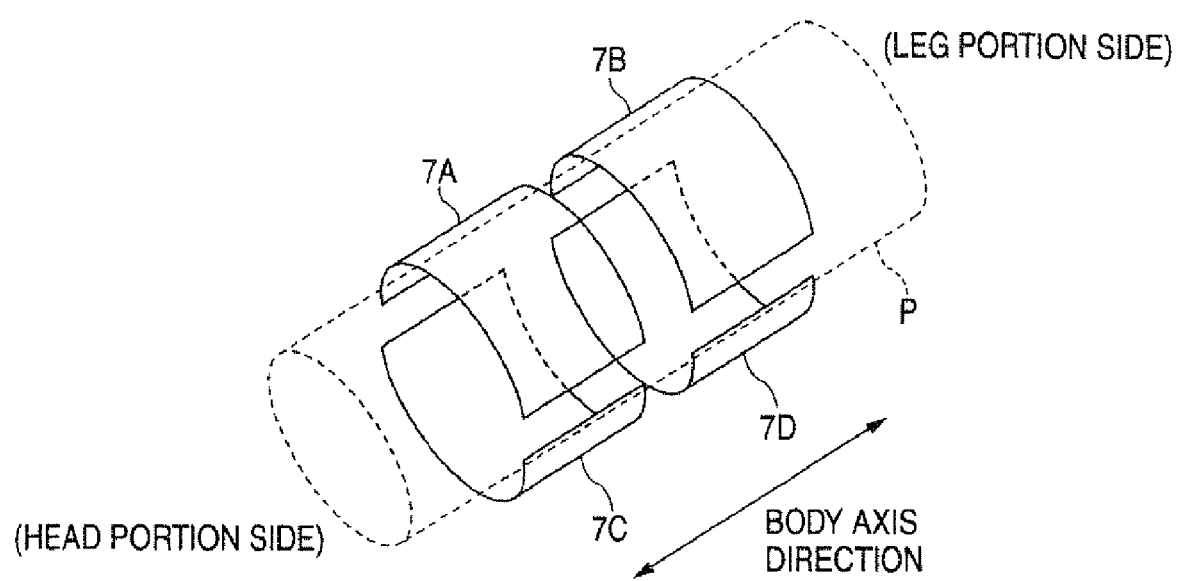
FIG. 8 is a view for explaining a coil arrangement in accordance with a modified example of the second embodiment mode.

In the above coil arrangement, as shown in FIG. 8, it is also possible to construct an arrangement of four element coils in which element coils 7A to 7D are respectively divisionally arranged in the vertical direction (direction from a head portion to a leg portion) on the back side and the abdominal wall side of the abdominal part. In this case, since the movement of the upper side (head portion side) of the abdominal part corresponding to the vicinity of the diaphragm is large, separate corrections are preferably respectively made with respect to the four element coils. Thus, the correction effect is large with respect to the images of a coronal face and a sagittal face.

Further, it is also possible to adopt an arranging construction of 1+4 coils in which an independent surface coil in accordance with the first embodiment mode and the above four element coils are combined and arranged. In this case, the movement of the upper side (head portion side) of the abdominal part corresponding to the vicinity of the diaphragm is large. Accordingly, the separate corrections may be also respectively made with respect to the four element coils of the divisional arrangement. Thus, a large correction effect is obtained with respect to the coronal face and the sagittal face.

Further, the image pickup part may be also set to a portion except for the abdominal part. When movement components of the image pickup part can be separated to a certain extent from the beginning between mutual signals outputted from the coil elements forming the multi-coil, the image pickup part except for the abdominal part may be also set. For example, when the image pickup part is the heart, it is known that the movements in the lower portion and the upper portion of the heart are nonlinear by the movement of the breathing property even in the same heartbeat phase. In this case, plural upper, lower, left and right surface coils are arranged so as to surround the heart from the body wall to execute the image pickup using the multi-coil in accordance with this second embodiment mode. Thus, each surface coil can detect the moving degree in a separating state in accordance with its coil sensitivity. Accordingly, the technique in accordance with this second embodiment mode can be executed.

In the pickup image of the abdominal part, the effect of the case extending the ghost from the abdominal wall side to the back side is also already confirmed by a simulation executed by the present inventors.

In the measurement of the spatial distribution of the movement using the multi-coil, the average shift amount of the position may be arithmetically calculated from the navi echo outputted by each coil element, and may be also used in the correction. In accordance with such a construction, the correction can be made even when no information relative to the position relation of the coil is identified. Thus, generation application can be performed irrespective of parts and coil modes.

Third Embodiment Mode

A magnetic resonance imaging device in accordance with a third embodiment mode is executed by combining processing based on the multi-coil (i.e., the construction explained in the above second embodiment mode), and the division of the moving component using the window processing using the image processing (i.e., the construction explained in the above first embodiment mode). Namely, in the magnetic resonance imaging device in accordance with the third embodiment mode, the window processing is performed with respect to each image from each coil element and data are divided to subdivide the moving component.

Figure 9:
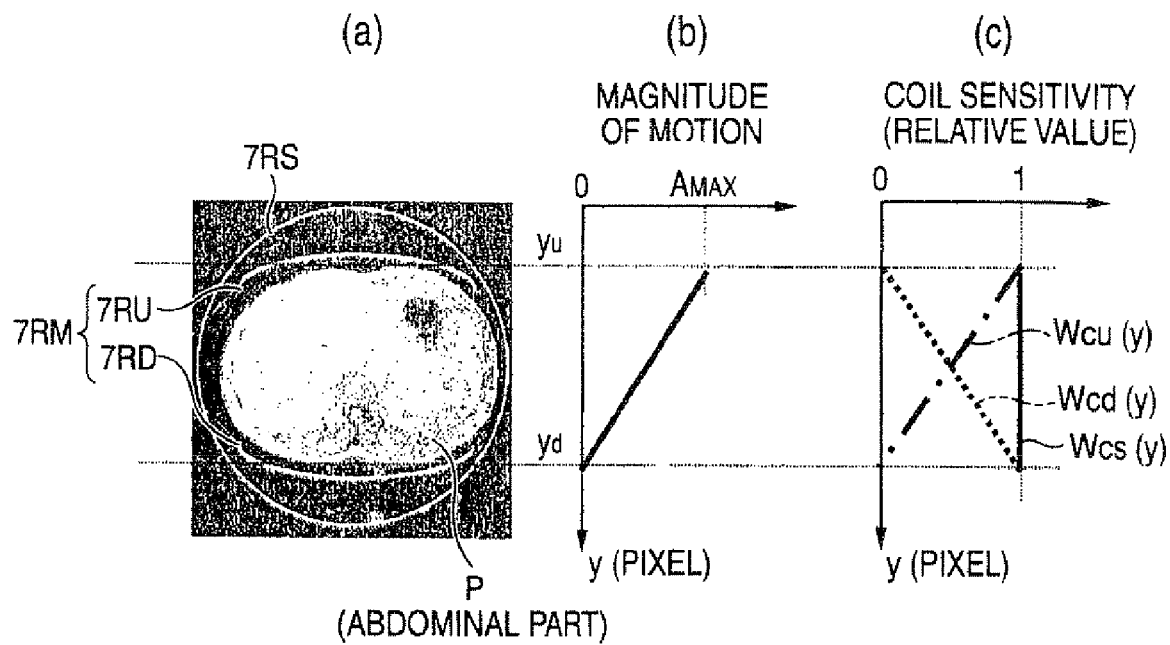
FIG. 9 is a view showing a single coil and a multi-coil used as a signal receiving RF coil, their sensitivity profiles and the magnitude of a non-rigid body motion of the detected body in a magnetic resonance imaging device in accordance with a third embodiment mode of the present invention.

FIG. 9 is a view showing the single coil and the multi-coil used as the signal receiving RF coil, their sensitivity profiles and the magnitude of non-rigid body motion of the detected body in the magnetic resonance imaging device in accordance with the third embodiment mode of the present invention.

As shown in FIG. 9(a), in the third embodiment mode, similar to the second embodiment mode shown in FIG. 7(a), a multi-coil 7RM is used as the signal receiving RF coil. As shown in FIG. 9(a), in the multi-coil 7RM two surface coils 7RU, 7RD are set to element coils. The surface coils 77RU, 7RD are respectively oppositely arranged on the back side and the abdominal wall side of the abdominal part of the detected body P. Further, a sleeve-shaped single coil 7RS is also arranged as the signal receiving RF coil so as to cover the detected body P in accordance with necessity. One or both of the single coil 7RS and the multi-coil 7RM can be arbitrarily used as the RE coil for signal reception.

FIG. 9(b) shows the magnitude of the non-rigid body motion in the abdominal part of the detected body P. The ordinate axis of FIG. 9(b) shows the position y [pixel] of image data shown in FIG. 9(a), and the abscissa axis shows the magnitude A(y) [pixel] of the movement in the pixel y.

As shown by the solid line A(y) within FIG. 9, it is supposed that the movement forms a first order distribution of the y-direction between $y_u$ and $y_d$. Namely, it is supposed that the magnitude A(y) of the movement is a maximum value Amax in $y_u$, and is 0 in $y_d$.

FIG. 9(c) shows respective normalized sensitivity distributions Wcu(y), Wcd(y), Wcs(y) of the respective surface coils 77RU, 7RD and the single coil 7RS in the y-direction. The ordinate axis of FIG. 9(c) shows the position y[pixel] of the image data shown in FIG. 9(a), and the abscissa axis shows respective normalized sensitivity distributions Wcu(y), Wcd (y), Wcs(y) of the respective surface coils 77RU, 7RD and the single coil 7RS in the y-direction.

As shown in FIG. 9(c), similar to the movement distribution, sensitivity distributions Wcu(y), Wcd(y) of the respective surface coils 77RU, 7RD are respectively set to a first order distribution in the y-direction. The sensitivity distribution Wcs(y) of the single coil 7RS is constantly set in the y-direction.

The k-space data collected by such respective surface coils 77RU, 7RD or single coil 7RS can be divided into plural areas by the window function. In particular, the k-space data collected by the two surface coils 77RU, 7RD are divided into two areas in hardware. Therefore, one or both of the respective areas can be further divided into plural areas in software by using the window function. Further, the k-space data collected by the single coil 7RS can be divided into an arbitrary number of areas in software by using the window function. For example, the k-space data collected by the single coil 7RS can be divided into two portions or three portions in software by using the window function similar to that of the first embodiment mode.

Figure 10:
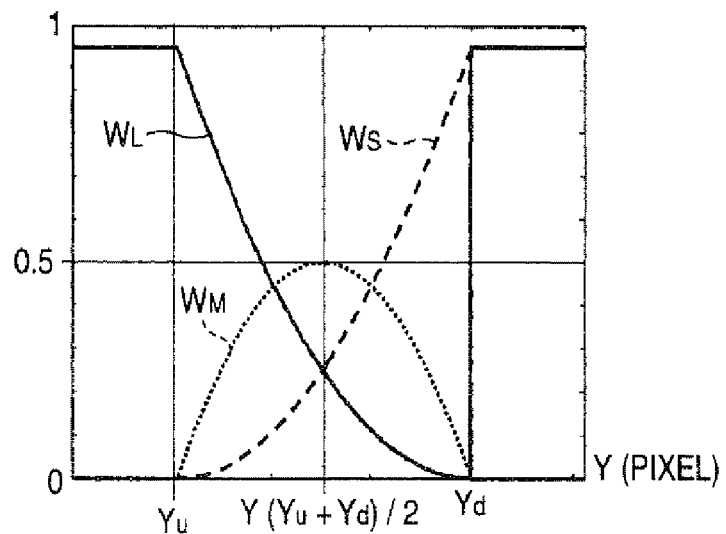
FIG. 10 is a view showing the window function when each k-space data collected by using two surface coils having a sensitivity distribution similar to a one-dimensional movement distribution as shown in FIG. 9 are divided into two areas so that these data are equivalently divided into three portions.

FIG. 10 is a view showing the window function when each of the k-space data collected by using the two surface coils 77RU, 7RD having sensitivity distributions similar to the one-dimensional moving distribution as shown in FIG. 9 is divided into two areas so that the k-space data are equivalently divided into three portions.

In FIG. 10, the axis of ordinate shows the values of window functions $W_L(y)$, $W_M(y)$, $W_S(y)$ and the axis of abscissa shows pixel positions of the y-direction shown in FIG. 9. Two k-space data collected by the two surface coils 77RU, 7RD using the three window functions $W_L(y)$, $W_M(y)$, $W_S(y)$ shown in FIG. 10 can be divided into three areas constructed by a larger area L, a medium area X and a smaller area S of the movement. The correction of intensity according to the magnitude of the movement can be made with respect to the k-space data of each divided area.

Namely, the k-space data divided into two portions in hardware by the two surface coils 7RU, 7RD are further divided into two areas in software by using the window function. Further, one portion of the areas can be synthesized such that the k-space data included in two medium areas of the movement among the four areas are included in a single area. Thus, one portion of the k-space data divided and collected by the plural element coils is synthesized with another portion and may also form the areas.

It is not limited to the plural k-space data divided in hardware by the plural element coils, but one portion of the k-space data once divided by the window function is similarly synthesized with another portion and the correction may be then made. The k-space data can be divided into predetermined desirable ununiform plural areas by using a more standard window function by performing synthesis processing of one portion of the k-space data before the correction, and the processing can be easily performed.

Each window function shown in FIG. 10 can be calculated from the moving distribution W(y) and the sensitivity distribution Wc(y) of the surface coils 7RU, 7RD respectively normalized by the following Formulas.

$$W_L(y) = Wc(y) * W(y) \quad\quad \text{[Formula 16]}$$
$$\cong [W(y)]^2 \quad (\text{if } Wc(y) \cong W(y))$$
$$W_M(y) = Wc(y) * [1 - W(y)] + [1 - Wc(y)] * W(y)$$
$$\cong 2 * [W(y) * \{1 - W(y)\}] \quad (\text{if } Wc(y) \cong W(y))$$
$$W_S(y) = 1 - W_L(y) - W_M(y)$$
$$\cong \{1 - W(y)\}^2 \quad (\text{if } Wc(y) \cong W(y))$$

Similar to the case for dividing the k-space data into three portions in software in the first embodiment mode, respective image data Pimg.u(x,y), Pimg.d(x,y) of the real space obtained by the two surface coils 77RU, 7RD are multiplied by the above window functions $W_L(y)$, $W_M(y)$, $W_S(y)$, and three image data $P_L(x,y)$, $P_M(x,y)$, $P_S(x,y)$ of the larger area, the medium area and the smaller area of the movement are generated. The two-dimensional inverse Fourier transform is performed with respect to each generated image data so that k-space data $S_L(Kx,Ky)$, $S_M(Kx,Ky)$, $S_S(Kx,Ky)$ divided into three areas in accordance with the magnitude of the movement can be obtained.

Further, with respect to the respective k-space data $S_L(Kx,Ky)$, $S_M(Kx,Ky)$, $S_S(Kx,Ky)$, the phase correction is executed at different intensities in accordance with the magnitude of the movement. The two-dimensional Fourier transform is performed with respect to k-space data $S_{img.cor}(Kx,Ky)$ provided by synthesizing the respective k-space data $S_{L.cor}(Kx,Ky)$, $S_{M.cor}(Kx,Ky)$, $S_S(Kx,Ky)$ after the phase correction. Thus, image data $P_{img.cor}(x,y)$ of the real space after the correction can be obtained.

Thus, in accordance with the third embodiment mode, the k-space data can be divided in hardware and software by using the plural element coils and the window function. Accordingly, both merits obtained by the first embodiment mode and the second embodiment mode can be given. Further, the k-space data are easily divided into predetermined desirable areas by simple processing and the correction of intensity according to the magnitude of the movement can be then made by synthesizing one portion of the k-space data once divided in hardware and software.

Figure 11:
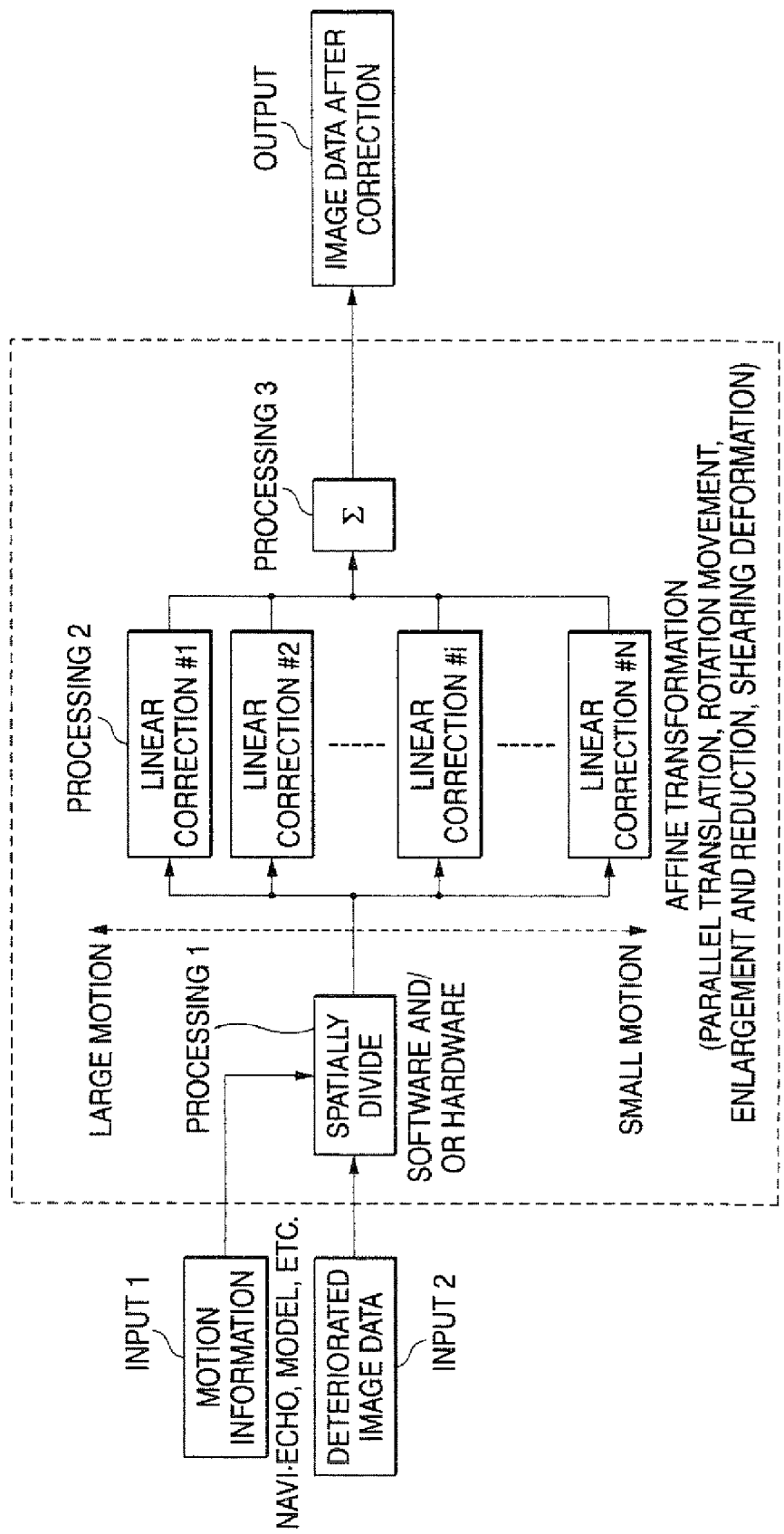
FIG. 11 is a view for explaining the principle of correction processing in each embodiment mode of the present invention.

A common principle of the correction processing of data in each embodiment node mentioned above will be generalized and explained. FIG. 11 shows the principle of the correction processing explained in each of the above embodiment modes.

First, information Input 1 of the movement of the non-rigid body is acquired by a certain method. For example, the movement may be measured from the navi echo, and the information Input 1 of the movement may be also obtained by forming a model. Next, image data Input 2 spatially deteriorated by the movement are spatially divided into plural components in accordance with the magnitude of the movement by using the information input 1 of the movement. Thus, plural k-space data respectively divided from each image data are obtained. This division (processing 1) of the k-space data may be performed in software by the window function, and may be also performed in hardware by using the multi-coil. Further, the k-space data divided in hardware by using the multi-coil may be also further divided in software by the window function.

Next, with respect to each component #i(1≦i≦N) of the k-space data divided into N-portions, a linear correction is made by linear transformation according to the magnitude of the movement (processing 2). Affine transformation (parallel translation), a rotating movement (rotation), enlargement and reduction (scaling) and shearing deformation (shear) are included in this linear transformation. Namely, the linear correction of stronger intensity is made with respect to a larger component of the movement. In contrast to this, the linear correction of weaker intensity is made with respect to a smaller component of the movement. With respect to the small component of the movement, a correction for setting the intensity to zero, i.e., a non-correction may be also set. Next, synthesis processing (processing 3) of each component of the k-space data after the correction is performed. Thereafter, image data Output after the entire correction are obtained by FT processing from the k-space data after the synthesis.

Figure 12:
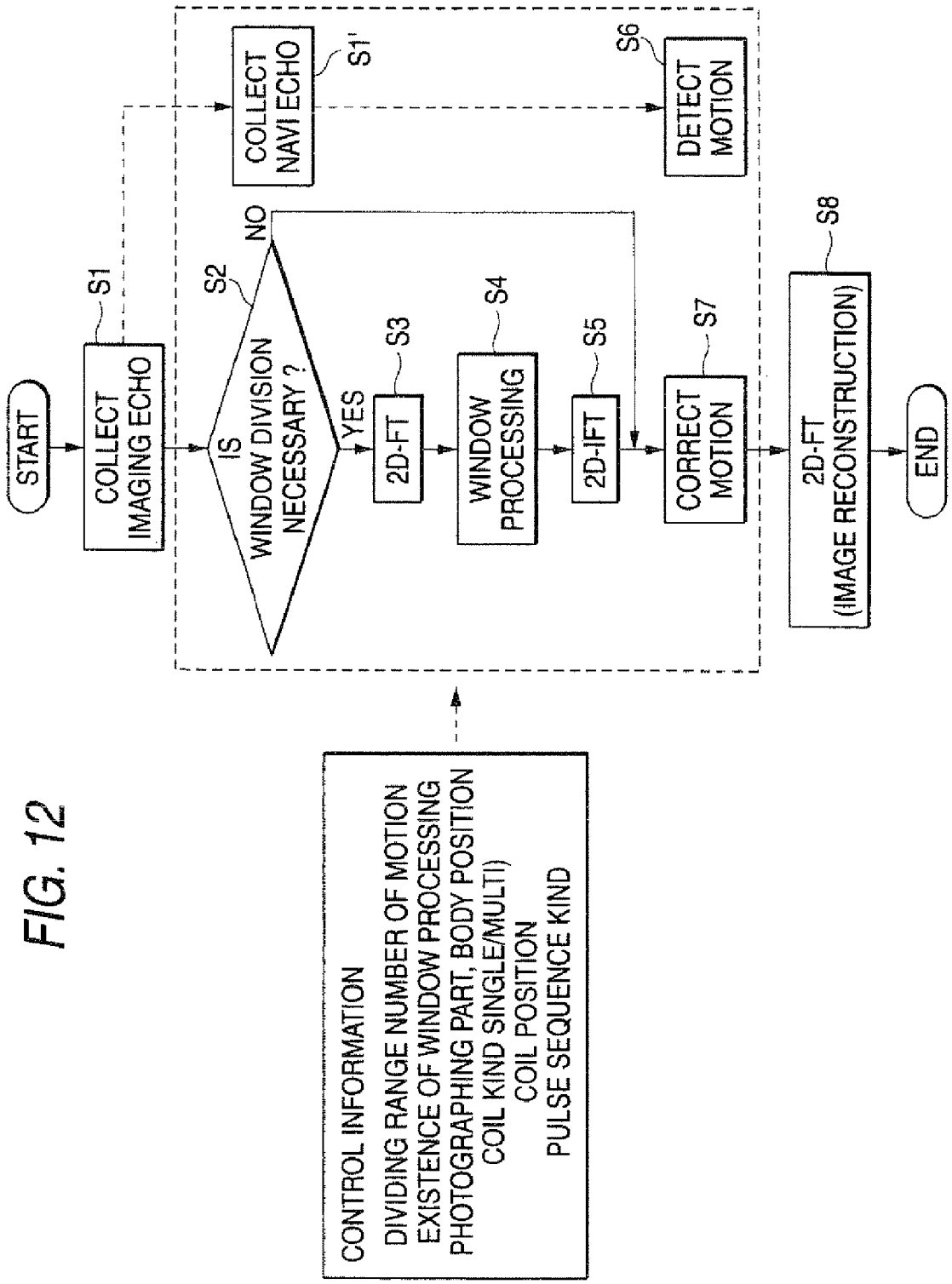
FIG. 12 is a schematic flow chart showing the procedure of processing common to the respective embodiment modes of the present invention.

The flow of the correction processing explained in each of the above embodiment modes is generalized and is shown in FIG. 12.

First, an image pickup part is scanned and imaged by the magnetic resonance imaging device, and echo data are collected (step S1). Navi echo data are collected together with this collection of the echo data, or are independently collected (step S1'). Data already collected may be also adopted in these echo data and navi echo data.

Next, such processing is entrusted to the arithmetic unit 10 of the magnetic resonance imaging device. Namely, an image reconstruction for also performing the correction processing according to the nonlinear movement of the abdominal part, etc. in the present invention is executed by the arithmetic unit 10 on the basis of various kinds of control information (a dividing area number of the movement, the existence of window processing, the image pickup part, a body position, the kind of coil (the single coil or the multi-coil), a coil arranging position, the kind of pulse sequence, etc.).

First, the arithmetic unit 10 judges whether software data division according to the moving degree is required or not (step S2). This judgment is made in consideration of the kind of a used signal receiving RE coil, the coil arranging position, etc.

When this judgment is YES, the two-dimensional Fourier transform (step S3: see processing c of FIG. 5), the window processing (step S4: see processing d of FIG. 5), the two-dimensional inverse Fourier transform processing (step S5: see processings e, f of FIG. 5), the detection of movement information in the r-space (step S6: see processings g, h of FIG. 5), the correction of deterioration due to the nonlinear movement of data of the k-space (step S7: see processing i of FIG. 5), and image generation using the two-dimensional Fourier and addition processing (step S8: see processings j, k of FIG. 5) explained in the above first embodiment mode are executed.

In contrast to this, when the judgment in the step S2 is NO, processing using the multi-coil explained in the above second embodiment mode as the signal receiving RF coil is executed. Namely, the processings of steps S3 to S5 are omitted, and the detection of movement information in the r-space (step S6: see processings d, e of FIG. 7), the correction of deterioration due to the nonlinear movement of data of the k-space (step S7: see processing f of FIG. 7), and image generation using the two-dimensional Fourier and addition processing (step S8: see processings g, h of FIG. 7) are directly executed.

Collection data spatially influenced by the nonlinear movement, or data spatially directly reflecting the nonlinear movement are collected along such a flow. A nonlinear component is replaced with a sum of linear components. It is then possible to reconstruct an MR image from which the influence of the nonlinear movement of the image pickup part is reliably removed at high speed by a small number of comparatively simple processings.

In recent years, as can be seen in the above non-patent literature 8, the following technique is reported in the field of the magnetic resonance imaging with respect to the heart. Namely, in this technique, a three-dimensional position of the diaphragm is calculated in real time from the navi echo monitored just before, and inclining magnetic field intensity and an RF frequency are controlled so that a slab face three-dimensionally follows in conformity with the movement of the heart, and the motion artifact and defocusing are reduced. This technique is an excellent method since no after-treatment is required and there is no image deterioration if it is limited to the affine transformation (parallel translation) as linear transformation, the enlargement and reduction (scaling), and the enlargement and reduction of the shearing deformation (shear).

When this technique is compared with the technique of the present invention, the shift due to the nonlinear movement can be first corrected as well as the linear transformation in the technique of the present invention. Namely, in the position shift due to the movement, there is the predominance of being also applicable to the spatial distribution of a high order unable in the linear transformation. Further, in the technique of the present invention, the division is performed after the image reconstruction before the correction even when the window processing is required. Accordingly, the arithmetic calculation becomes simple although it is after-treatment. Further, after the collection is terminated, a corrected image can be instantly outputted. Further, when the multi-coil is used, the arithmetic calculation is further simplified. If the navigation of the movement in a shot unit is executed just before the present imaging, there is also a predominance property able to perform the correction processing in real time.

In each of the above embodiment modes, the explanation has been made with respect to the one-dimensional correction processing, i.e., a case in which the moving direction is only the y-direction and amplitude shows a one-dimensional distribution. However, the measurement (detection) of movement information and its correction processing may be also three-dimensionally performed in each of the x, y and z directions. In particular, the movement information can be measured on the basis of the phase distribution in the k-space or the shift of the position of at least one direction in the r-space.

Here, a case for three-dimensionally correcting the movement of the non-rigid body will be explained When the motion of the non-rigid body is generalized and both the direction and the magnitude of the shift due to the movement are different every place and every time, i.e., when the direction and displacement of the shift are a four-dimensional distribution, it is sufficient to set a weight function for dividing data to a high order in accordance with the distribution of the shift due to the movement. Concretely, when the displacing direction is mixed in the three directions $\Delta X$, $\Delta Y$, $\Delta Z$, the window functions are separately calculated with respect to the three directions in accordance with the magnitudes of the separate independent movements of the three directions constructed by the x, y and z directions measured or presumed every shot. Thus, the division is performed in accordance with the magnitude of the movement, and the correction is additionally executed.

For example, the window function is made every magnitude of the movement (L, M, S in the three divisions) every direction of the movement (x, y, z in the 3D space). After the correction is made every component divided by the magnitude of the movement with respect to each direction, the correction of entire data can be made by making an additional calculation. An algorithm example of this case is shown below.

Figure 13:
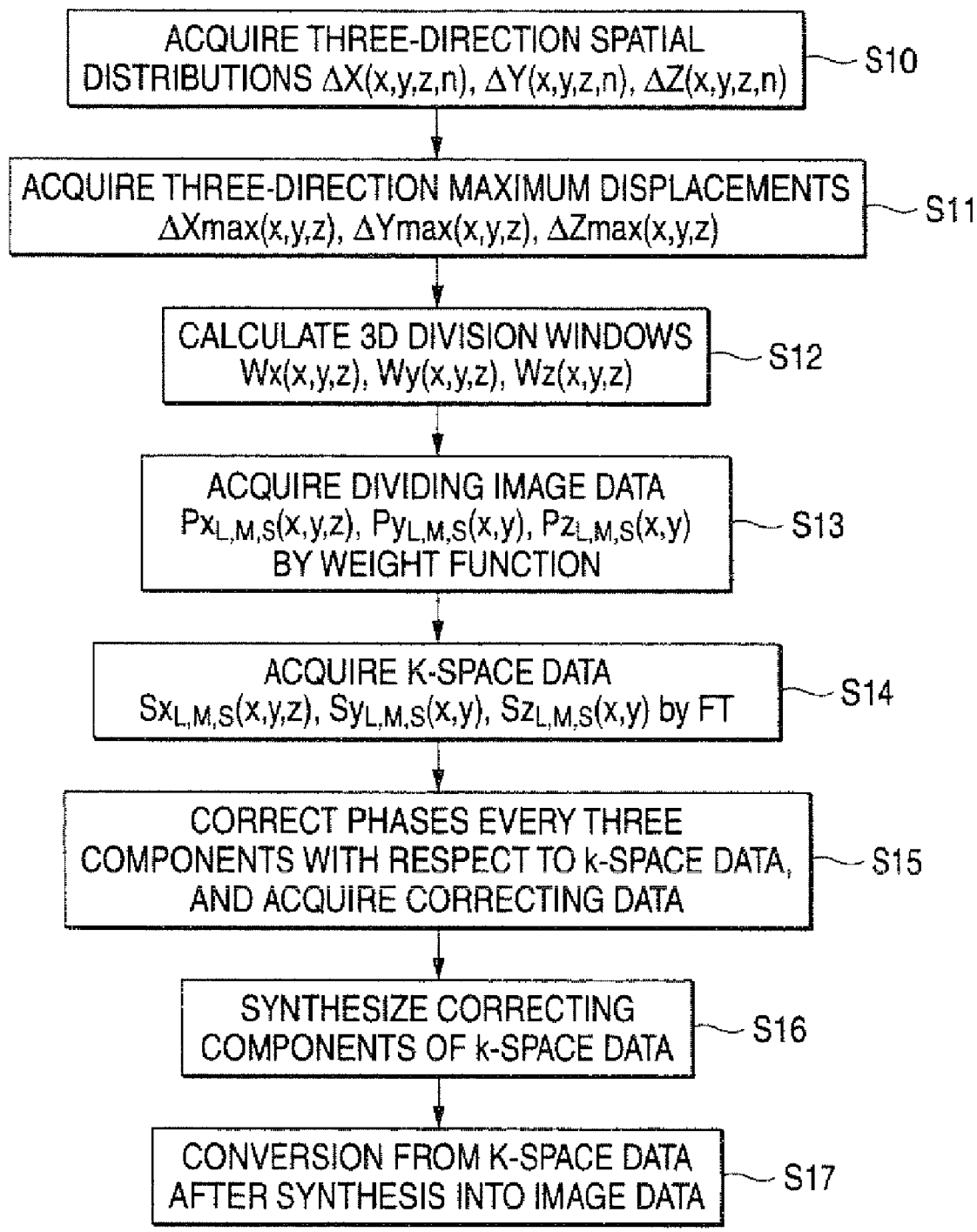
FIG. 13 is a flow chart showing a procedure when the movement of a non-rigid body is three-dimensionally corrected by the present invention.
Figure 14:
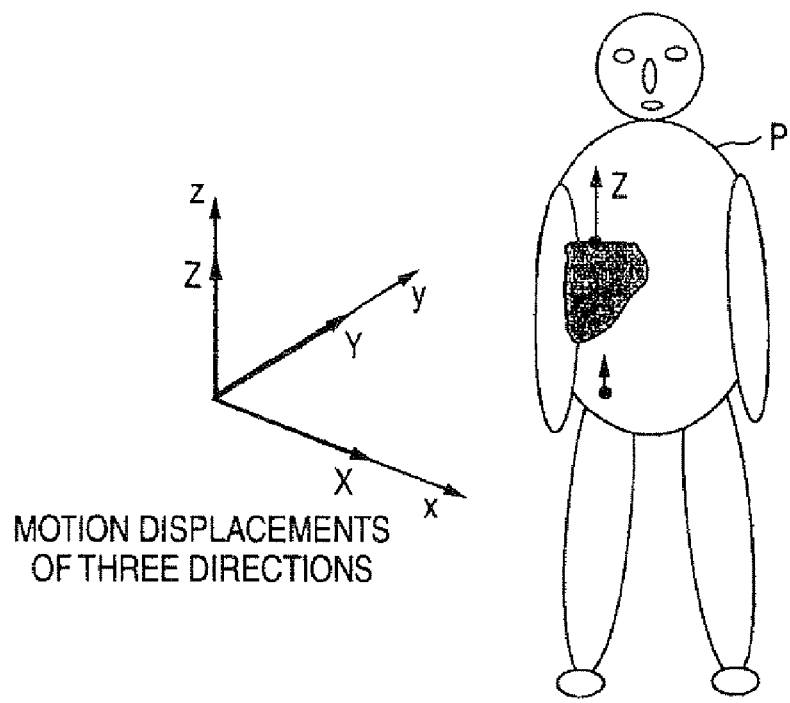
FIG. 14 is a view showing an example of a moving direction seen from the y-direction when there is a three-dimensional movement of the non-rigid body in the detected body.
Figure 15:
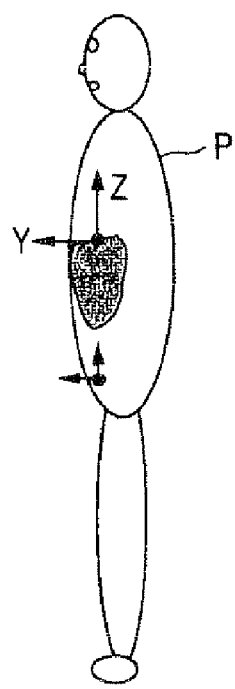
FIG. 15 is a view showing the moving direction seen from the x-direction of the non-rigid body in the detected body shown in FIG. 14.

FIG. 13 is a flow chart showing the procedure of a case for three-dimensionally correcting the movement of the non-rigid body by the present invention. In FIG. 13, a symbol provided by adding a numeral to S shows each step of the flow chart. FIG. 14 is a view showing an example of a moving direction seen from the y-direction when there is a three-dimensional movement of the non-rigid body in the detected body P. FIG. 15 is a view showing the moving direction seen from the x-direction of the non-rigid body in the detected body P shown in FIG. 14.

First, in a step S10, spatial distributions $\Delta X(x,y,z,n)$, $\Delta Y(x,y,z,n)$, $\Delta Z(x,y,z,n)$ every three directions of a displacement vector (X,Y,Z) (see FIG. 14) from a certain reference every shot n in the shift of a certain position (x,y,z) due to the movement are obtained.

Next, in a step S11, maximum displacements $\Delta X_{max}(x,y,z)$, $\Delta Y_{max}(x,y,z)$, $\Delta Z_{max}(x,y,z)$ in the three directions in the 3D space are calculated by the following formulas.

$$\Delta X_{max}(x,y,z)=\max[\Delta X(x,y,z,n)]$$

$$\Delta Y_{max}(x,y,z)=\max[\Delta Y(x,y,z,n)]$$

$$\Delta Z_{max}(x,y,z)=\max[\Delta Z(x,y,z,n)] \quad \text{[Formula 17]}$$

Next, in a step S12, respective 3D division window functions (weight functions) $Wx(x,y,z)$, $Wy(x,y,z)$, $Wz(x,y,z)$ of the three directions are calculated by the following formulas.

$$Wx(x,y,z)=\Delta X(x,y,z)/\Delta X_{max}(x,y,z)$$

$$Wy(x,y,z)=\Delta Y(x,y,z)/\Delta Y_{max}(x,y,z)$$

$$Wz(x,y,z)=\Delta Z(x,y,z)/\Delta Z_{max}(x,y,z) \quad \text{[Formula 18]}$$

Next, in a step S13, image data $P(x,y,z)$ of the real space are divided by the window function of each direction by the following formulas with respect to the three direction components. Indices of L (large), M (medium) and S (small) are set to be added every magnitude of the movement.

$$Px_{L,M,S}(x,y,z)=P(x,y,z)Wx_{L,M,S}(x,y,z)$$

$$Py_{L,M,S}(x,y)=P(x,y,z)Wy_{L,M,S}(x,y,z)$$

$$Pz_{L,M,S}(x,y)=P(x,y,z)Wz_{L,M,S}(x,y,z) \quad \text{[Formula 19]}$$

Next, in a step S14, as shown in the following formulas, the inverse Fourier transform is performed with respect to the divided image data $Px_{L,M,S}(x,y,z)$, $Py_{L,M,S}(x,y)$, $Pz_{L,M,S}(x,y)$ so that k-space data $Sx_{L,M,S}(x,y,z)$, $Sy_{L,M,S}(x,y)$, $Sz_{L,M,S}(x,y)$ are obtained.

$$Sx_{L,M,S}(k_x,k_y,k_z)=IFT[Px_{L,M,S}(x,y,z)]$$

$$Sy_{L,M,S}(k_x,k_y,k_z)=IFT[Py_{L,M,S}(x,y,z)]$$

$$Sx_{L,M,S}(k_x,k_y,k_z)=IFT[Py_{L,M,S}(x,y,z)] \quad \text{[Formula 20]}$$

Next, in a step S15, the phase correction is made with respect to the k-space data every three components as shown in the following formulas.

Correction of Movement Maximum Portion $$Sx.cor_L(k_x,k_y,k_z)=Sx._L(k_x,k_y,k_z).\exp[-i\phi x_{max}(k_x,k_y,k_z)]$$

$$Sy.cor_L(k_x,k_y,k_z)=Sy._L(k_x,k_y,k_z).\exp[-i\phi y_{max}(k_x,k_y,k_z)]$$

$$Sz.cor_L(k_x,k_y,k_z)=Sz._L(k_x,k_y,k_z).\exp[-i\phi z_{max}(k_x,k_y,k_z)] \quad \text{[Formula 21]}$$

Correction of Movement Medium Portion $$Sx.cor_M(k_x,k_y,k_z)=Sx._M(k_x,k_y,k_z).\exp[-i\phi x_{max}(k_x,k_y,k_z)/2]$$

$$Sy.cor_M(k_x,k_y,k_z)=Sy._M(k_x,k_y,k_z).\exp[-i\phi y_{max}(k_x,k_y,k_z)/2]$$

$$Sz.cor_M(k_x,k_y,k_z)=Sz._M(k_x,k_y,k_z).\exp[-i\phi z_{max}(k_x,k_y,k_z)/2]$$

In this case, the following formulas are formed.

$$\phi x_{max}(k_x,k_y,k_z)=2\pi k_x \Delta X_{max}(x,y,z)/K_x$$

$$\phi y_{max}(k_x,k_y,k_z)=2\pi k_y \Delta Y_{max}(x,y,z)/K_y$$

$$\phi z_{max}(k_x,k_y,k_z)=2\pi k_z \Delta Z_{max}(x,y,z)/K_z$$

Next, in a step S16, as shown in the following formulas, correction components $Sx.cor_L(k_x,k_y,k_z)$, $Sy.cor_L(k_x,k_y,k_z)$, $Sz.cor_L(k_x,k_y,k_z)$, $Sx.cor_M(k_x,k_y,k_z)$, $Sy.cor_M(k_x,k_y,k_z)$, $Sz.cor_M(k_x,k_y,k_z)$ and non-correction components $Sx._S(k_x,k_y,k_z)$, $Sy._S(k_x,k_y,k_z)$, $Sx._S(k_x,k_y,k_z)$ of the k-space data are synthesized. Concretely, the respective movement components in the correction components are added every three directions, and components Sx.cor, Sy.cor, Sz.cor of the three directions after the addition are then further added.

$$Sx.cor=Sx.cor_L(k_x,k_y,k_z)+Sx.cor_M(k_x,k_y,k_z)+Sx._S(k_x,k_y,k_z)$$

$$Sy.cor=Sy.cor_L(k_x,k_y,k_z)+Sy.cor_M(k_x,k_y,k_z)+Sy._S(k_x,k_y,k_z)$$

$$Sz.cor=Sz.cor_L(k_x,k_y,k_z)+Sz.cor_M(k_x,k_y,k_z)+Sz._S(k_x,k_y,k_z)$$

$$S.cor=Sx.cor+Sy.cor+Sz.cor \quad \text{[Formula 22]}$$

Thus, the k-space data S.cor three-dimensionally corrected can be obtained.

Further, in a step S17, it is possible to obtain 3D image data P.cor in which the correction of the three-dimensional movement is made by 3DFT of the k-space data after the synthesis.

In each of the above embodiment modes, the technique for detecting the movement information is not limited to a technique using the navi echo collected by applying the inclining magnetic field as a navigation pulse, but may be also set to a technique using external optical, magnetic and mechanical sensors. In this case, even when no measurement can be made by such a sensor until the spatial distribution of the movement, the movement of only the abdominal wall is monitored, and the spatial distribution may be also presumed in combination with a modeling result of a body movement distribution measured or presumed in advance. Thus, since the measurement parallel to the data collection of the magnetic resonance imaging can be made, it is also possible to cope with high speed imaging of the heart etc.

Further, it is also possible to perform the execution by a combination in which control on the fly of high frequency, the inclining magnetic field, etc. is performed with respect to only a component able to be corrected by the linear transformation, and only the remaining nonlinear components of the second order or more are corrected by the technique in the present invention.

Further, in the above correction processing, when a measured phase error exceeds a predetermined limit value able to be coped as the device, threshold value processing may be also performed at this limit value.

On the other hand, in each of the above embodiment modes, when the image data to be corrected, or required image data are one portion of a divided area, the divided image data after the correction are not necessarily synthesized.

In addition, in each of the above embodiment modes, after the image data in the r-space are divided, plural k-space data are generated by converting each divided image data. However, data of a separate space may be generated from the data of the r-space by conversion able to take over the nature of the data of the r-space, and the k-space data may be also generated by converting the data of this separate space. Further, conversely, the conversion is once performed from the data of the r-space to the data of another space obtained by conversion able to take over the nature of the data of the k-space, and the k-space data may be also generated from the data of this another space.

Typical effects common to the above embodiment modes and modified examples can be summarized as follows.

If the spatial distribution of the one-dimensional (projection) or two-dimensional/three-dimensional movement (the position shift or the phase shift) can be measured, the phase or a signal value of data deteriorated by the nonlinear movement can be comparatively simply corrected by arithmetically calculating a linear sum of at least two different correction data. In the case of the correction of the position shift, processing can be performed at high speed since the measurement and the phase correction in the same wave number in the k-space are made in comparison with a case in which the measurement of the position shift and the correction processing are performed by crossing a voxel in the r-space. The correction in the r-space is suitable in the case of the phase correction within the voxel. However, in comparison with the case processed every voxel, the arithmetic calculation is simple and can be made at high speed.

Further, even when no spatial distribution of the movement is strictly measured, the entire spatial distribution is presumed as a model even in the nonlinear case from a whole average and measurement data of the movement of a typical portion such as the abdominal wall, etc. Accordingly, when the measurement is made by the navi echo for simplifying a measuring system, the sequence is shortened and a high speed operation can be performed. For example, if it is an axial section of the abdominal part, it can be supposed that the position shift due to the movement is gradually increased from the back to the abdominal wall side.

Further, even when the single coil is used, it is sufficient to reconstruct data by a division number of the k-space data. Accordingly, the high speed operation can be performed in comparison with the correction in the r-space. In addition, when the image of the abdominal part is picked up by using the multi-coil, the echo data can be directly acquired. Accordingly, correction accuracy is improved, and the high speed operation can be further performed since no window division is required.

Here, a fault image in the abdominal part of the detected body P obtained by making the correction by the present invention is shown in comparison with a conventional fault image obtained without making the correction.

Figure 16:
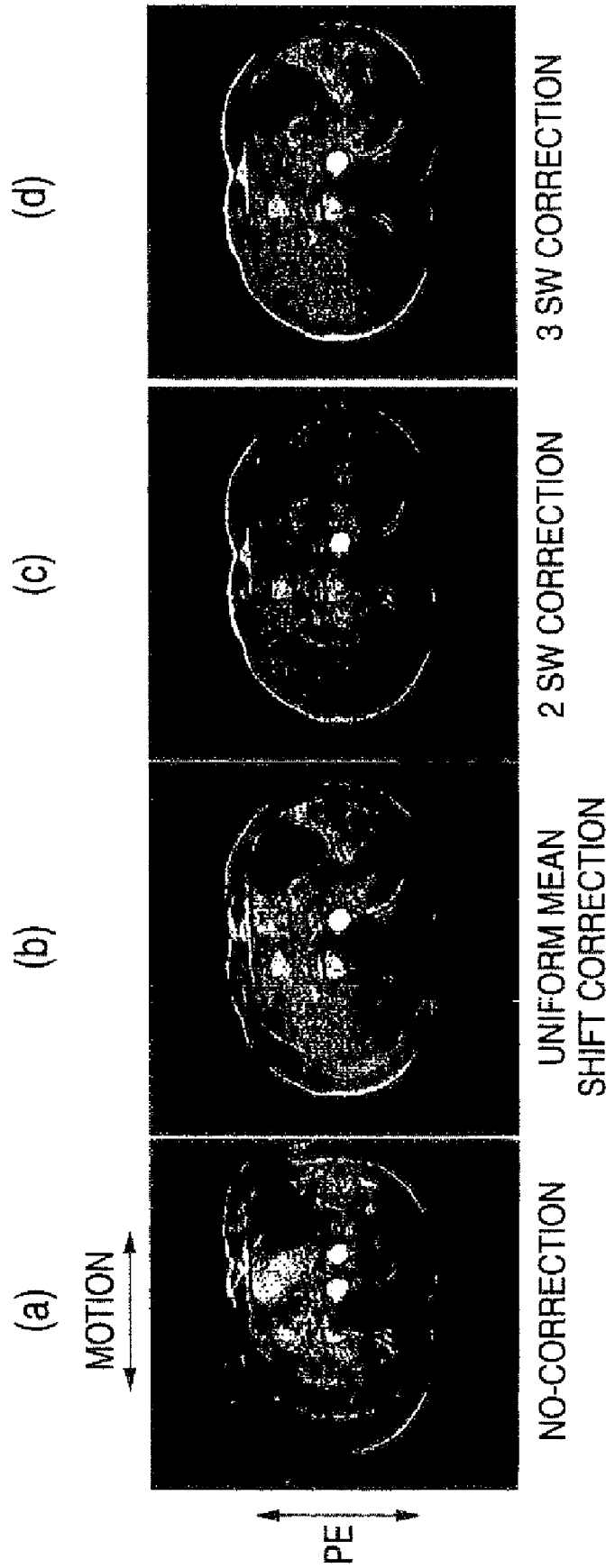
FIG. 16 is a view showing a fault image obtained by dividing and correcting the k-space data in software using the single coil by the present invention when there is a movement of the non-rigid body having a one-dimensional distribution in a direction perpendicular to a phase encode direction.

FIG. 16 is a view showing a fault image obtained by dividing and correcting the k-space data in software by using the single coil by the present invention when there is a movement of the non-rigid body having a one-dimensional distribution in a direction perpendicular to the phase encode (PE) direction.

FIG. 16($a$) shows an image obtained without making the correction. FIG. 16($b$) shows an image obtained by a conventional uniform mean shift correction. FIG. 16($c$) shows an image obtained by respectively linearly correcting each k-space data divided into two portions in software by the present invention. FIG. 16($d$) shows an image obtained by respectively linearly correcting each k-space data divided into three portions in software by the present invention.

When the conventional uniform mean shift correction is made with respect to the image before the correction shown in FIG. 16($a$), it can be the that the correction is insufficient although the ghost of the central portion in the forward-backward direction of the detected body P conformed to a correcting amount is reduced as shown in FIG. 16($b$).

On the other hand, as shown in FIG. 16($c$), when data are divided into two portions in software by the present invention and are respectively linearly corrected at different intensities, a reduction of SNR and correction insufficiency of the ghost are seen in an intermediate (intermediate in the forward-backward direction of the detected body P) portion of a window. However, it can be confirmed that the ghost is notably reduced in comparison with the image obtained by the conventional uniform mean shift correction. Further, as shown in FIG. 16($d$), when data are divided into three portions in software by the present invention and are respectively linearly corrected at different intensities, the reduction of SNR and the ghost in the intermediate portion in the forward-backward direction of the detected body P are sufficiently corrected, and a notable correction effect can be confirmed.

Figure 17:
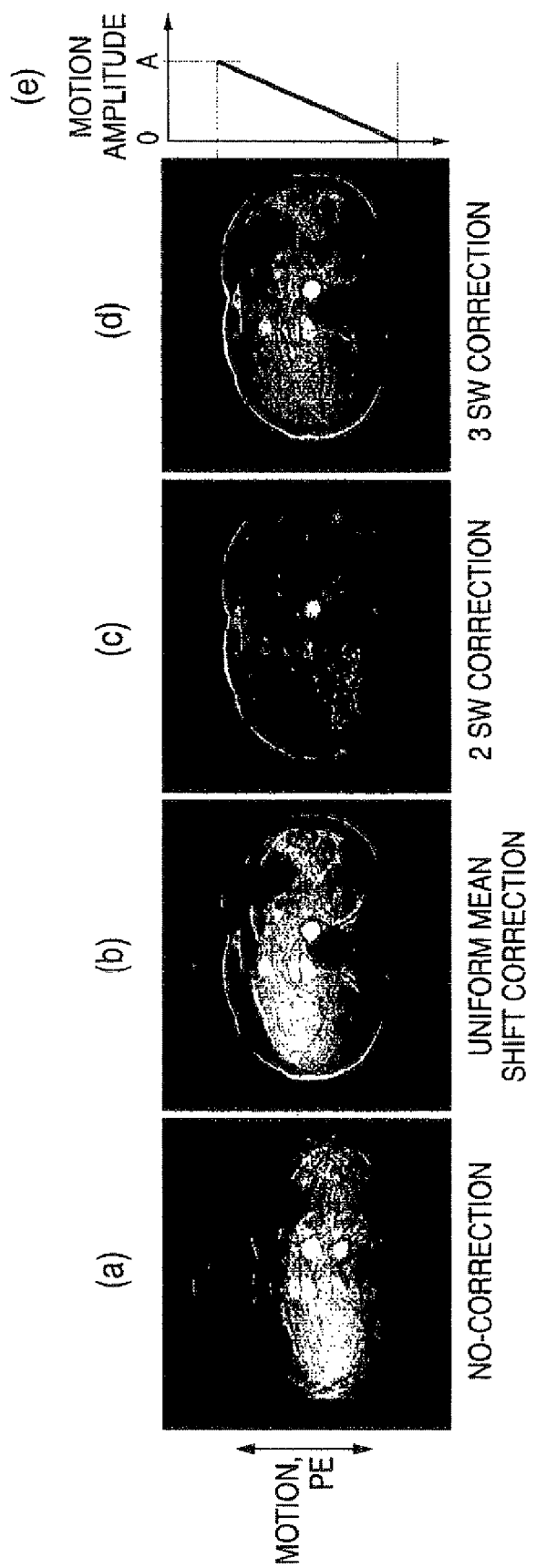
FIG. 17 is a view showing a fault image obtained by dividing and correcting the k-space data in software using the single coil by the present invention when there is a movement of the non-rigid body having the one-dimensional distribution in a PE direction.

FIG. 17 is a view showing a fault image obtained by dividing and correcting the k-space data in software by using the single coil by the present invention when there is a movement of the non-rigid body having a one-dimensional distribution in the PE direction.

FIG. 17($a$) shows an image obtained without making the correction. FIG. 17($b$) shows an image obtained by the conventional uniform mean shift correction. FIG. 17($c$) shows an image obtained by respectively linearly correcting each k-space data divided into two portions in software by the present intention. FIG. 17($d$) shows an image obtained by respectively linearly correcting each k-space data divided into three portions in software by the present invention. FIG. 17($e$) is a view showing a one-dimensional distribution of the movement (ordinate axis: pixel position, and abscissa axis: normalized magnitude of movement).

When the conventional uniform mean shift correction is made with respect to the image before the correction shown in FIG. 17($a$), it is seen that the ghost including a newly generated ghost is generated before and after in the same degree as shown in FIG. 17($b$).

On the other hand, as shown in FIG. 17($c$), it can be confirmed that the ghost is reduced when data are divided into two portions in software by the present invention, and are linearly corrected at different intensities. Further, as shown in FIG. 17($d$), when data are divided into three portions in software by the present invention and are linearly corrected at different intensities, the ghost is further reduced. It can be further confirmed that the reduction of a signal in an intermediate portion of the abdominal wall and the back is improved.

FIG. 18 is a view showing a fault image obtained by dividing and correcting the k-space data by including an air portion in software using the single coil by the present invention when there is a movement of the non-rigid body having a one-dimensional distribution in the PE direction.

FIG. 18(a) shows an image obtained by respectively linearly correcting each k-space data divided into two portions by including the air portion in software by the present invention. FIG. 18(b) shows an image obtained by respectively linearly correcting each k-space data divided into three portions by including the air portion in software by the present invention.

In the air portion, the ghost flying from a moving portion is dominant. Therefore, when the image data are corrected as maximum (L) data in the movement by including the air portion, the ghost is reduced as shown in FIGS. 18(a) and 18(b) in comparison with FIGS. 17(c) and 17(d) including no air portion.

FIG. 19 is a view showing a fault image when there is a movement of the nor-rigid body having a one-dimensional distribution in the PE direction. The k-space data divided into two portions in hardware by using the multi-coil having two element coils by the present invention are further divided into two portions in software by using the window function. The fault image is obtained by linearly correcting the k-space data equivalently divided into three portions.

FIG. 19(a) shows an image obtained by making the linear correction without dividing the k-space data divided into two portions in hardware by the two element coils in software. FIG. 19(b) shows an image in which the k-space data divided into two portions in hardware by the two element coils are further divided into two portions in software, and the image is obtained by correcting the k-space data equivalently divided into three portions.

FIG. 19(a) shows the image obtained by correcting only a dominant data side of the movement among the data obtained by the two element coils. However, in comparison with the image of FIG. 17(c) obtained by correcting data divided into two portions in software by using the single coil, the ghost of the back side spatially distantly flying is reduced. Further, FIG. 19(b) shows the image obtained by correcting data equivalently divided into three portions by dividing data obtained by the two element coils into two portions in software. In accordance with FIG. 19(b), the reduction of SNR of the intermediate portion is further improved. It can be also confirmed that a most preferable correcting effect is obtained in comparison with other images shown in FIGS. 16(a), (b), (c), (d), FIGS. 17(a), (b), (c), (d), FIGS. 18(a), (b) and FIG. 19(a).

In corrections with respect to an image before the correction, an image obtained by the uniform mean shift correction, and an image in a case of the movement one-dimensionally distributed in the read-out (RO) direction perpendicular to the PE direction, there is no difference between the case using the single coil and the case using the multi-coil.

The present invention is not limited to the descriptions of the above embodiment modes, but can be embodied by modifying constructional elements in the scope not departing from its gist at an embodiment stage. Further, various kinds of inventions can be formed by a suitable combination of plural constructional elements disclosed in the above embodiment modes. For example, some constructional elements may be deleted from all the constructional elements shown in the embodiment modes. Further, constructional elements over different embodiment modes may be also suitably combined. When the image of the heart is formed, this image is influenced by both the movement provided by a heartbeat and the movement of the breathing property. However, a method for monitoring a breathing period by the navi echo and dynamically controlling the position of a slice face in addition to heartbeat gating is adopted.

The invention claimed is:

1. An image data correcting device comprising at least one programmed computer connected to execute program code which includes:
   a movement information acquiring section for acquiring movement information showing a spatial distribution of the magnitude of a movement in the real space of an image pickup part of a detected body;
   a correcting section for making a correction different from that of a second area in a first area of image data of the image pickup part of said detected body collected by a scan of magnetic resonance imaging on the basis of said movement information; and
   a synthesizing section for synthesizing respective image data of said first area and said second area corrected by said correcting section,
   wherein said correcting section is configured to make corrections different from each other and including a non-correction with respect to two areas or more obtained by mutually synthesizing one portion of at least three areas in said image data of said image pickup part.

2. The image data correcting device according to claim 1, wherein said correcting section is constructed so as to perform linear correction processing according to a spatially ununiform deteriorating degree of said image data generated by the movement of said image pickup part.

3. The image data correcting device according to claim 1, wherein said synthesizing section is constructed so as to synthesize the image data after a first correction in said first area, and the image data after a second correction different from said first correction in said second area.

4. The image data correcting device according to claim 1, wherein said synthesizing section is constructed so as to synthesize the image data after the correction in said first area, and uncorrected image data in said second area.

5. The image data correcting device according to claim 1, wherein said movement information acquiring section has a navigator echo collecting section for collecting an echo signal for a navigator when data for imaging are collected from said image pickup part, and also has a movement information generating section for processing said echo signal and generating said movement information.

6. The image data correcting device according to claim 1, wherein said movement information acquiring section has:
   a sensor for detecting the movement of said image pickup part optically or by air pressure; and
   a movement information generating section for processing a signal detected by said sensor and generating said movement information.

7. The image data correcting device according to claim 1, wherein said correcting section is constructed so as to respectively make different corrections with respect to three or more areas of said image data.

8. The image data correcting device according to claim 1, wherein said movement information acquiring section has:
   a navigator echo collecting section for collecting an echo signal for a navigator when data for imaging are collected from said image pickup part;
   a processing information acquiring section for obtaining processing information including average values of the amplitude and phase of the movement of each part from said echo signal;

a profile acquiring section for acquiring an entire profile of said spatial distribution by using a predetermined model; and a movement information generating section for generating said movement information on the basis of said profile and said processing information.

9. The image data correcting device according to claim 1, wherein said movement information acquiring section has:
a navigator echo collecting section for collecting an echo signal for a navigator in one of a data read-out direction and a phase encode direction caused by the imaging when data for imaging are collected from said image pickup part;
a projection data generating section for processing said echo signal and generating projection data; and
a movement information generating section for using said projection data as said movement information.

10. The image data correcting device according to claim 1, wherein said movement information acquiring section has:
a navigator echo collecting section for collecting an echo signal for a navigator when data for imaging are collected from said image pickup part; and
a movement information generating section for calculating a shift of one of a phase distribution of a k-space of said echo signal and a position of at least one direction of an r-space as said movement information.

11. The image data correcting device according to claim 1, wherein an image data collecting section for collecting said image data by using a single signal receiving radio frequency (RF) coil is arranged.

12. The image data correcting device according to claim 1, wherein said correcting section is constructed so as to substantially generate plural image data by multiplying said image data in said image pickup part by plural window functions having weight distributions different from each other.

13. The image data correcting device according to claim 1, wherein said correcting section is constructed so as to perform linear correction processing with respect to one of a position shift due to said movement of said respective image data in said first area and said second area, and a phase shift within a voxel.

14. The image data correcting device according to claim 1, wherein said correcting section is constructed so as to perform linear correction processing shown by one of a mean shift as a zeroth order of one of the phase and the position, and affine transformation.

15. The image data correcting device according to claim 1, wherein said movement information acquiring section is constructed so as to acquire the movement information showing a three-dimensional spatial distribution, and said correcting section is constructed so as to three-dimensionally make the correction on the basis of the movement information showing said three-dimensional spatial distribution.

16. The image data correcting device according to claim 1, wherein said movement information acquiring section is constructed so as to acquire the movement information showing a spatial distribution of the magnitude of the movement of a non-rigid body.

17. The image data correcting device according to claim 1, wherein said movement information acquiring section is constructed so as to use the spatial distribution of the magnitude of a predetermined movement in said image pickup part.

18. The image data correcting device according to claim 17, wherein said movement information acquiring section sets an abdominal part to said image pickup part, and is constructed such that a distribution substantially linearly increased from a back side of said abdominal part to an abdominal wall side of said abdominal part with respect to the amplitude of the movement of each part in a direction directed from said back side to the abdominal wall side is used as said spatial distribution.

19. The image data correcting device according to claim 1, wherein an image data collecting section for collecting said image data by providing a sensitivity distribution according to the magnitude of the movement of said image pickup part in advance is arranged.

20. The image data correcting device according to claim 19, wherein said image data collecting section is constructed so as to collect said image data by using the multi-coil having plural element coils of sensitivity distributions different from each other.

21. The image data correcting device according to claim 20, wherein said image data collecting section sets an abdominal part to said image pickup part, and has two surface coils respectively arranged on a back side and an abdominal wall side of said abdominal part as said plural element coils.

22. The image data correcting device according to claim 20, wherein said image data collecting section sets the abdominal part to said image pickup part, and has plural surface coils respectively arranged on the back side and the abdominal wall side as said plural element coils, and arranged in plural places along a direction directed from a head portion to a leg portion on at least one of said back side and said abdominal wall side.

23. The image data correcting device according to claim 20, wherein said correcting section is constructed so as to substantially generate plural image data by multiplying one portion or all portions of the plural image data collected by using said plural element coils by plural window functions having weight distributions different from each other.

24. The image data correcting device according to claim 1, wherein said correcting section is constructed so as to obtain said two areas or more by mutually synthesizing one portion of plural image data collected by using plural element coils.

25. The image data correcting device according to claim 1, wherein said correcting section is constructed so as to substantially generate said three image data or more as a synthesizing object by multiplying said image data in said image pickup part by plural window functions having weight distributions different from each other.

26. The image data correcting device according to claim 1, wherein an image data collecting section for executing said scan by using a pulse sequence constructed by a pulse series based on one of (a) a spin warp method, (b) a spiral method, and (c) radial method in a pulse series of one of a multi-shot type and a single type is arranged.

27. An image data correcting method comprising:
using a magnetic resonance imaging (MRI) system having at least one programmed computer processor connected to execute program code which, when executed:
acquires movement information showing a spatial distribution of the magnitude of a movement in the real space of an image pickup part of a detected body;
makes a correction different from that of a second area in a first area of image data of the image pickup part of said detected body collected by a scan of magnetic resonance imaging on the basis of said movement information; and
synthesizes the respective corrected image data of said first area and said second area,
wherein said correction makes corrections different from each other and including a non-correction with respect to two areas or more obtained by mutually synthesizing one portion of at least three areas in said image data of said image pickup part.

28. An image data correcting method comprising:
using a magnetic resonance imaging (MRI) system having at least one programmed computer processor connected to execute program code which, when executed:
makes a correction different from that of a second area in a first area of image data of an image pickup part of a detected body collected by a scan of magnetic resonance imaging on the basis of movement information showing a spatial distribution of the magnitude of a movement in the real space of said image pickup part; and
synthesizes the respective corrected image data of said first area and said second area,
wherein said correction makes corrections different from each other and including a non-correction with respect to two areas or more obtained by mutually synthesizing one portion of at least three areas in said image data of said image pickup part.

29. A magnetic resonance imaging device comprising at least one programmed computer connected to execute program code which includes:
a movement information acquiring section for acquiring movement information showing a spatial distribution of the magnitude of a movement in the real space of an image pickup part of a detected body;
an image data collecting section for collecting image data of the image pickup part of said detected body by a scan of magnetic resonance imaging;
a correcting section for making a correction different from that of a second area in a first area of said collected image data on the basis of said movement information; and
a synthesizing section for synthesizing the respective image data of said first area and said second area corrected by said correcting section,
wherein said correcting section is configured to make corrections different from each other and including a non-correction with respect to two areas or more obtained by mutually synthesizing one portion of at least three areas in said image data of said image pickup part.

30. An image data correcting device comprising at least one programmed computer connected to execute program code which includes:
an image data collecting section for collecting image data of an image pickup part of a detected body by a scan of magnetic resonance imaging;
a correcting section for making a correction different from that of a second area in a first area of said collected image data on the basis of movement information showing a spatial distribution of the magnitude of a movement in the real space of said image pickup part; and
a synthesizing section for synthesizing the respective image data of said first area and said second area corrected by said correcting section,
wherein said correcting section is configured to make corrections different from each other and including a non-correction with respect to two areas or more obtained by mutually synthesizing one portion of at least three areas in said image data of said image pickup part.

* * * * *